US011365255B2

(12) United States Patent
Yuan et al.

(10) Patent No.: US 11,365,255 B2
(45) Date of Patent: *Jun. 21, 2022

(54) PD-1 ANTIBODY, ANTIGEN-BINDING FRAGMENT THEREOF, AND MEDICAL APPLICATION THEREOF

(71) Applicants: Suzhou Suncadia Biopharmaceuticals Co., Ltd., Jiangsu (CN); Jiangsu Hengrui Medicine Co., Ltd., Jiangsu (CN); Shanghai Hengrui Pharmaceutical Co., Ltd., Shanghai (CN)

(72) Inventors: Jijun Yuan, Shanghai (CN); Xiangdong Qu, Shanghai (CN); Jufang Lin, Shanghai (CN); Xin Ye, Shanghai (CN); Guoqing Cao, Jiangsu (CN); Weikang Tao, Jiangsu (CN); Lianshan Zhang, Jiangsu (CN); Lei Zhang, Shanghai (CN); Li Yang, Shanghai (CN)

(73) Assignees: Suzhou Suncadia Biopharmaceuticals Co., Ltd., Suzhou (CN); Jiangsu Hengrui Medicine Co., Ltd., Lianyungang (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 247 days.

This patent is subject to a terminal disclaimer.

(21) Appl. No.: 16/426,001

(22) Filed: May 30, 2019

(65) Prior Publication Data
US 2019/0309069 A1 Oct. 10, 2019

Related U.S. Application Data

(63) Continuation of application No. 15/103,758, filed as application No. PCT/CN2014/091090 on Nov. 14, 2014, now Pat. No. 10,344,090.

(51) Int. Cl.
*A61K 39/00* (2006.01)
*C07K 16/28* (2006.01)

(52) U.S. Cl.
CPC .... *C07K 16/2818* (2013.01); *A61K 2039/505* (2013.01); *C07K 2317/20* (2013.01); *C07K 2317/24* (2013.01); *C07K 2317/33* (2013.01); *C07K 2317/56* (2013.01); *C07K 2317/565* (2013.01); *C07K 2317/567* (2013.01); *C07K 2317/73* (2013.01); *C07K 2317/76* (2013.01); *C07K 2317/92* (2013.01)

(58) Field of Classification Search
CPC .............................................. A61K 2039/505
See application file for complete search history.

(56) References Cited

U.S. PATENT DOCUMENTS

| 5,629,204 | A | 5/1997 | Honjo et al. |
|---|---|---|---|
| 5,698,520 | A | 12/1997 | Honjo et al. |
| 6,632,927 | B2 | 10/2003 | Adair et al. |
| 6,808,710 | B1 | 10/2004 | Wood et al. |
| 6,884,879 | B1 | 4/2005 | Baca et al. |
| 7,029,674 | B2 | 4/2006 | Carreno et al. |
| 7,488,802 | B2 | 2/2009 | Collins et al. |
| 7,521,051 | B2 | 4/2009 | Collins et al. |
| 7,563,869 | B2 | 7/2009 | Honjo et al. |
| 7,595,048 | B2 | 9/2009 | Honjo et al. |
| 7,851,598 | B2 | 12/2010 | Davis |
| 7,998,479 | B2 | 8/2011 | Honjo et al. |
| 8,008,449 | B2 | 8/2011 | Korman et al. |
| 8,168,757 | B2 | 5/2012 | Finnefrock et al. |
| 8,246,955 | B2 | 8/2012 | Honjo et al. |
| 8,287,856 | B2 | 10/2012 | Li et al. |
| 8,354,509 | B2 | 1/2013 | Carven et al. |
| 8,460,886 | B2 | 6/2013 | Shibayama et al. |
| 8,709,416 | B2 | 4/2014 | Langermann et al. |
| 8,728,474 | B2 | 5/2014 | Honjo et al. |
| 8,735,553 | B1 | 5/2014 | Li et al. |
| 8,779,105 | B2 | 7/2014 | Korman et al. |
| 8,956,619 | B2 | 2/2015 | Ostrand-Rosenberg |
| 9,102,728 | B2 | 8/2015 | Tyson |
| 9,828,428 | B2 * | 11/2017 | Ma ................... G01N 33/57492 |
| 9,896,513 | B2 * | 2/2018 | Krogh ....................... A61P 7/04 |
| 10,344,090 | B2 * | 7/2019 | Yuan .................. C07K 16/2818 |
| 10,786,567 | B2 * | 9/2020 | Li .......................... A61K 47/12 |

(Continued)

FOREIGN PATENT DOCUMENTS

CA 2143491 A1 9/1995
CN 1080311 A 1/1994
(Continued)

OTHER PUBLICATIONS

Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Winkler et al. (J. Immunol. Oct. 15, 2000; 165 (8): 4505-4514).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*

(Continued)

*Primary Examiner* — Stephen L Rawlings
(74) *Attorney, Agent, or Firm* — Ice Miller LLP

(57) ABSTRACT

The present invention provides a human PD-1 antibody, an antigen-binding fragment thereof, and medical use thereof, and further provides a chimeric antibody and humanized antibodies comprising a complementarity-determining region (CDR) of the antibody, a pharmaceutical composition comprising the human PD-1 antibody and the antigen-binding fragment thereof, and use of the antibody in preparing medicines for treating diseases or disorders.

12 Claims, 3 Drawing Sheets

Specification includes a Sequence Listing.

(56) References Cited

U.S. PATENT DOCUMENTS

| | | | |
|---|---|---|---|
| 2005/0033030 A1* | 2/2005 | Lo | A61K 51/1093 530/388.15 |
| 2010/0151492 A1 | 6/2010 | Ahmed et al. | |
| 2011/0171215 A1 | 7/2011 | Davis et al. | |
| 2011/0171220 A1 | 7/2011 | Davis | |
| 2011/0177088 A1 | 7/2011 | Olive et al. | |
| 2011/0229461 A1 | 9/2011 | Tyson | |
| 2011/0293607 A1 | 12/2011 | Labrijn et al. | |
| 2012/0014947 A1 | 1/2012 | Fu | |
| 2012/0076805 A1 | 3/2012 | Sharpe et al. | |
| 2012/0100139 A1 | 4/2012 | Thompson et al. | |
| 2012/0114651 A1 | 5/2012 | de Wildt et al. | |
| 2012/0251537 A1 | 10/2012 | Ahmed et al. | |
| 2012/0269806 A1 | 10/2012 | Sykes | |
| 2013/0095098 A1 | 4/2013 | Tyson | |
| 2013/0108651 A1 | 5/2013 | Carven et al. | |
| 2013/0109843 A1 | 5/2013 | Carven et al. | |
| 2013/0156774 A1 | 6/2013 | Kuchroo et al. | |
| 2013/0202623 A1 | 8/2013 | Chomont et al. | |
| 2013/0291136 A1 | 10/2013 | Freeman et al. | |
| 2013/0309250 A1 | 11/2013 | Cogswell et al. | |
| 2013/0345406 A1 | 12/2013 | Van De Winkel et al. | |
| 2014/0044738 A1 | 2/2014 | Langermann et al. | |
| 2014/0147411 A1 | 5/2014 | Pollack et al. | |
| 2014/0155678 A1 | 6/2014 | Zeng et al. | |
| 2014/0178370 A1 | 6/2014 | Freeman et al. | |
| 2014/0220021 A1 | 8/2014 | Shibayama et al. | |
| 2015/0086541 A1 | 3/2015 | Aguilar-Cordova | |
| 2015/0266962 A1* | 9/2015 | Ma | C07K 16/2866 424/178.1 |
| 2016/0032012 A1* | 2/2016 | Krogh | A61K 39/3955 424/133.1 |
| 2016/0376367 A1* | 12/2016 | Yuan | A61P 35/00 424/139.1 |
| 2018/0339045 A1* | 11/2018 | Li | A61K 47/02 |
| 2019/0161540 A1* | 5/2019 | Gearing | C07K 1/165 |
| 2020/0040078 A1* | 2/2020 | Sun | C07K 16/2818 |
| 2021/0015858 A1* | 1/2021 | Cui | C07K 16/2809 |

FOREIGN PATENT DOCUMENTS

| | | | | |
|---|---|---|---|---|
| CN | 1259961 A | | 7/2000 | |
| CN | 101355965 A | | 1/2009 | |
| CN | 101663323 A | | 3/2010 | |
| CN | 102203125 A | | 9/2011 | |
| CN | 102282265 A | | 12/2011 | |
| CN | 102740887 A | | 10/2012 | |
| CN | 102892785 A | | 1/2013 | |
| CN | 104974253 A | | 10/2015 | |
| CN | 104987421 A | | 10/2015 | |
| CN | 105085680 A | | 11/2015 | |
| CN | 105175545 A | | 12/2015 | |
| CN | 105754990 A | | 7/2016 | |
| CN | 109806393 A | * | 5/2019 | |
| EP | 1537878 A1 | | 6/2005 | |
| EP | 02172219 A1 | | 4/2010 | |
| JP | 4409430 B2 | | 2/2010 | |
| JP | 5159730 B2 | | 3/2013 | |
| KR | 100391227 B1 | | 10/2003 | |
| WO | 0114557 A1 | | 3/2001 | |
| WO | 2004004771 A1 | | 1/2004 | |
| WO | 2006121168 A1 | | 11/2006 | |
| WO | 2008156712 A1 | | 12/2008 | |
| WO | 2009014708 A2 | | 1/2009 | |
| WO | 2009114335 A2 | | 9/2009 | |
| WO | 2010027827 A2 | | 3/2010 | |
| WO | 2010029434 A1 | | 3/2010 | |
| WO | 2010029435 A1 | | 3/2010 | |
| WO | 2010036959 A2 | | 4/2010 | |
| WO | 2010040105 A2 | | 4/2010 | |
| WO | 2010089411 A2 | | 8/2010 | |
| WO | 2010106051 A1 | | 9/2010 | |
| WO | 2011066342 A2 | | 6/2011 | |
| WO | 2011100841 A1 | | 8/2011 | |
| WO | 2011110604 A1 | | 9/2011 | |
| WO | 2011110621 A1 | | 9/2011 | |
| WO | 2011159877 A2 | | 12/2011 | |
| WO | 2012086346 A1 | | 6/2012 | |
| WO | 2012113064 A1 | | 8/2012 | |
| WO | 2012135408 A1 | | 10/2012 | |
| WO | 2012145493 A1 | | 10/2012 | |
| WO | 2013019906 A1 | | 2/2013 | |
| WO | 2013022091 A1 | | 2/2013 | |
| WO | 2013043647 A1 | | 3/2013 | |
| WO | 2013079945 A1 | | 6/2013 | |
| WO | 2013090552 A1 | | 6/2013 | |
| WO | 2013169388 A1 | | 11/2013 | |
| WO | 2013169693 A1 | | 11/2013 | |
| WO | 2013173223 A1 | | 11/2013 | |
| WO | 2013181452 A1 | | 12/2013 | |
| WO | 2014008218 A1 | | 1/2014 | |
| WO | 2014043708 A1 | | 3/2014 | |
| WO | 2014046983 A1 | | 3/2014 | |
| WO | 2014055648 A1 | | 4/2014 | |
| WO | 2014059251 A1 | | 4/2014 | |
| WO | 2014074852 A1 | | 5/2014 | |
| WO | WO-2014100542 A1 | * | 6/2014 | G16C 20/60 |
| WO | 2014107873 A1 | | 7/2014 | |
| WO | 2014127917 A1 | | 8/2014 | |
| WO | 2014145907 A1 | | 9/2014 | |
| WO | 2014158811 A1 | | 10/2014 | |
| WO | 2014159562 A1 | | 10/2014 | |
| WO | 2014161509 A1 | | 10/2014 | |
| WO | 2014193898 A1 | | 12/2014 | |
| WO | 2014194302 A2 | | 12/2014 | |
| WO | 2014195852 A1 | | 12/2014 | |
| WO | 2014206107 A1 | | 12/2014 | |
| WO | 2014209804 A1 | | 12/2014 | |
| WO | 2015016718 A1 | | 2/2015 | |
| WO | 2015023505 A1 | | 2/2015 | |
| WO | 2015024042 A1 | | 2/2015 | |
| WO | 2015026684 A1 | | 2/2015 | |
| WO | 2015035112 A1 | | 3/2015 | |
| WO | 2015035606 A1 | | 3/2015 | |
| WO | 2015036394 A1 | | 3/2015 | |
| WO | 2015038538 A1 | | 3/2015 | |
| WO | 2015042246 A1 | | 3/2015 | |
| WO | 2015048312 A1 | | 4/2015 | |
| WO | 2015050663 A1 | | 4/2015 | |
| WO | 2015058573 A1 | | 4/2015 | |
| WO | 2015069571 A1 | | 5/2015 | |
| WO | 2015069697 A2 | | 5/2015 | |
| WO | 2015069770 A1 | | 5/2015 | |
| WO | 2015075725 A1 | | 5/2015 | |
| WO | 2015081158 A1 | | 6/2015 | |
| WO | 2015085847 A1 | | 6/2015 | |
| WO | 2015088847 A1 | | 6/2015 | |
| WO | 2015094992 A1 | | 6/2015 | |
| WO | 2015094995 A2 | | 6/2015 | |
| WO | 2015094996 A2 | | 6/2015 | |
| WO | 2015095404 A2 | | 6/2015 | |
| WO | 2015095811 A2 | | 6/2015 | |
| WO | 2015095868 A1 | | 6/2015 | |
| WO | WO-2015085847 A1 | * | 6/2015 | A61P 35/00 |
| WO | 2015103072 A1 | | 7/2015 | |
| WO | 2015108907 A2 | | 7/2015 | |
| WO | 2015112800 A1 | | 7/2015 | |
| WO | 2015112900 A1 | | 7/2015 | |
| WO | 2015119923 A1 | | 8/2015 | |
| WO | 2015119930 A1 | | 8/2015 | |
| WO | 2015119944 A1 | | 8/2015 | |
| WO | 2015125159 A1 | | 8/2015 | |
| WO | 2015127158 A1 | | 8/2015 | |
| WO | 2015127501 A1 | | 9/2015 | |
| WO | 2015134605 A1 | | 9/2015 | |
| WO | 2015136541 A2 | | 9/2015 | |
| WO | 2015138920 A1 | | 9/2015 | |
| WO | 2015153639 A1 | | 10/2015 | |
| WO | 2015176033 A1 | | 11/2015 | |
| WO | 2015181331 A1 | | 12/2015 | |
| WO | 2015190538 A1 | | 12/2015 | |
| WO | 2015192068 A1 | | 12/2015 | |
| WO | 2015193352 A1 | | 12/2015 | |

(56) References Cited

FOREIGN PATENT DOCUMENTS

| | | |
|---|---|---|
| WO | 2015200119 A1 | 12/2015 |
| WO | 2016007513 A1 | 1/2016 |
| WO | 2016008976 A1 | 1/2016 |
| WO | 2016010879 A1 | 1/2016 |
| WO | 2016011357 A1 | 1/2016 |
| WO | 2016014148 A1 | 1/2016 |
| WO | 2016014688 A2 | 1/2016 |
| WO | 2016014799 A1 | 1/2016 |
| WO | 2016015685 A1 | 2/2016 |
| WO | 2016022813 A1 | 2/2016 |
| WO | 2016023960 A1 | 2/2016 |
| WO | 2016024228 A1 | 2/2016 |
| WO | 2016025645 A1 | 2/2016 |
| WO | 2016027764 A1 | 2/2016 |
| WO | 2016028656 A1 | 2/2016 |
| WO | 2016028672 A1 | 2/2016 |
| WO | 2016029073 A2 | 2/2016 |
| WO | 2016032927 A1 | 3/2016 |
| WO | 2016033555 A1 | 3/2016 |
| WO | 2016040238 A1 | 3/2016 |
| WO | 2016040880 A1 | 3/2016 |
| WO | 2016040892 A1 | 3/2016 |
| WO | 2016041945 A1 | 3/2016 |
| WO | 2016044207 A1 | 3/2016 |
| WO | 2016049641 A1 | 3/2016 |
| WO | 2016054555 A2 | 4/2016 |
| WO | 2016057841 A1 | 4/2016 |
| WO | 2016061286 A2 | 4/2016 |
| WO | 2016068801 A1 | 5/2016 |
| WO | 2016069727 A1 | 5/2016 |
| WO | 2016070001 A1 | 5/2016 |
| WO | 2016070051 A2 | 5/2016 |
| WO | 2016073704 A1 | 5/2016 |
| WO | 2016075099 A1 | 5/2016 |
| WO | 2016075174 A1 | 5/2016 |
| WO | 2016077397 A2 | 5/2016 |
| WO | 2016077553 A1 | 5/2016 |
| WO | 2016079050 A1 | 5/2016 |
| WO | 2016081384 A1 | 5/2016 |
| WO | 2016081947 A2 | 5/2016 |
| WO | 2016089873 A1 | 6/2016 |
| WO | 2016090070 A1 | 6/2016 |
| WO | 2016090300 A1 | 6/2016 |
| WO | 2016092419 A1 | 6/2016 |
| WO | 2016094273 A1 | 6/2016 |
| WO | 2016094377 A1 | 6/2016 |
| WO | 2016094456 A1 | 6/2016 |
| WO | 2016100561 A2 | 6/2016 |
| WO | 2016100882 A1 | 6/2016 |
| WO | 2016106159 A1 | 6/2016 |
| WO | 2016106302 A1 | 6/2016 |
| WO | 2016109310 A1 | 7/2016 |
| WO | 2016110593 A1 | 7/2016 |
| WO | 2016111645 A1 | 7/2016 |
| WO | 2016115345 A1 | 7/2016 |
| WO | 2016115480 A1 | 7/2016 |
| WO | 2016119308 A1 | 8/2016 |
| WO | 2016120789 A1 | 8/2016 |
| WO | 2016127179 A2 | 8/2016 |

OTHER PUBLICATIONS

Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Yu et al. (PLoS One. 2012; 7 (3): e33340; pp. 1-15).*
Chang et al. (Structure. Jan. 7, 2014; 22 (1): 9-21).*
Sula-Culang et al. (Front. Immunol. Oct. 2013; 4: 302; pp. 1-13).*
Ingram et al. (Proc. Natl. Acad. Sci. USA. Apr. 10, 2018; 115 (15): 3912-3917).*
Kipps et al. (J. Exp. Med. Jan. 1, 1985; 161 (1): 1-17).*
Pantelyushin et al. (Cancers (Basel). Feb. 2021; 13 (4): 785; pp. 1-18).*
Gura (Science. 1997; 278: 1041-1042).*
Dennis (Nature. Aug. 7, 2006; 442: 739-741).*
Nielsen et al. (Cell Immunol. Jun. 2005; 235 (2): 109-16).*
Ascierto, "Immunotherapies and novel combinations: the focus of advances in the treatment of melanoma," Cancer Immunol. Immunother, 4 pages (2014).
Barber et al., "Restoring function in exhausted CD8 T cells during chronic viral infection," Nature, vol. 439, pp. 682-687 (Feb. 2006).
Beiboer et al., "Guided Selection of a Pan Carcinoma Specific Antibody Reveals Similar Binding Characteristics yet Structural Divergence Between the Original Murine Antibody and its Human Equivalent," J. Mol. Biol., vol. 296, pp. 833-849 (2000).
Bender et al., "Safety of the PD-1 antibody Pembrolizumab in Patients with High Grade Adverse Events under Ipilimumab Treatment," Annals of Oncology Advance Access, 4 pages (Mar. 2016).
Benson et al., "The PD-1/PD-L1 axis modulates the natural killer cell versus multiple myeloma effect: a therapeutic target for CT-011, a novel monoclonal anti-PD-1 antibody," Blood, pp. 2286-2294 (2010).
Blank et al., "PD-L1/B7H-1 Inhibits the Effector Phase of Tumor Rejection by T Cell Receptor (TCR) Transgenic CD8+ T Cells," Cancer Res.,vol. 64, No. 3, pp. 1140-1145 (Feb. 2004).
Blank et al., "Contribution of the PD-L1/PD-1 pathway to T-cell exhaustion: an update on implications for chronic infections and tumor evasion," Cancer Immunol. Immunother., vol. 56, pp. 739-745 (2007).
Blank et al., "Interaction of PD-L1 on tumor cells with PD-1 on tumor-specific T cells as a mechanism of immune evasion: implications for tumor immunotherapy," Cancer Immunol. Immunothera. vol. 54, pp. 307-314 (2005).
Boils et al., "Use of the PD-1 pathway inhibitor nivolumab in a renal transplant patient with malignancy," Am. J. Transplant., 4 pages (2016).
Bryan et al., "Blocking tumor escape in hematologic malignancies: The anti-PD-1 strategy," Blood Reviews, pp. 1-8 (2014).
Callahan et al., "At the Bedside: CTLA-4- and PD-1-blocking antibodies in cancer immunotherapy," Journal of Leukocyte Biology, vol. 94, pp. 41-53 (Jul. 2013).
Carter et al., "PD-1:PD-L inhibitory pathway affects both CD4+ and CD8+ T cells and is overcome by IL-2," Eur. J. Immunol., vol. 32, No. 3, pp. 634-643 (2002).
Chen et al., "Anti-PD-1/PD-L 1 therapy of human cancer: past, present, and future," J. Clin. Invest., vol. 125, No. 9, pp. 3384-3391 (Sep. 2015).
Cheng et al., "Structure and Interactions of the Human Programmed Cell Death 1 Receptor," J. Bio. Chem., vol. 288, No. 17, pp. 11771-11785 (Apr. 2013).
Curis, "Overview and Path for Growth," Aurigene Strategic Collaboration, 13 slides (Jan. 21, 2015).
Dolan et al., "PD-1 Pathway Inhibitors: Changing the Landscape of Cancer Immunotherapy," Cancer Control, vol. 21, No. 3, pp. 231-237 (Jul. 2014).
Domling et al., "Programmed Death-1: Therapeutic Success after More than 100 Years of Cancer Immunotherapy," Angew. Chem. Int. Ed., vol. 53, pp. 2283-2288 (2014).
European Search Report dated Jun. 6, 2017 in EP Application No. 14868918.5.
FDA Report, "22 Case Studies Where Phase 2 and Phase 3 Trials Had Divergent Results," U.S. Food and Drug Administiation, 44 pages (Jan. 2017).
Fife et al., "The role of the PD-1 pathway in autoimmunity and peripheral tolerance," Annals of the New York Academy of Sciences, pp. 45-59 (2011).
Francisco et al., "The PD-1 Pathway in Tolerance and Autoimmunity," Immunol. Rev., vol. 236, pp. 219-242 (Jul. 2010).
Freeman et al., "Engagement of the PD-1 Immunoinhibitory Receptor by a Novel B7 Family Member Leads to Negative Regulation of Lymphocyte Activation," J. Exp. Med., vol. 192, No. 7, pp. 1027-1034 (Oct. 2000).

(56) References Cited

OTHER PUBLICATIONS

Freeman, G. J., "Structures of PD-1 with its ligands: Sideways and dancing cheek to cheek," PNAS, vol. 105, No. 30, pp. 10275-10276 (Jul. 2008).

Gatalica et al., "Programmed Cell Death 1 (PD-1) and its Ligand (PD-L1) in Common Cancers and Their Correlation with Molecular Cancer Type," Cancer Epidemiology, Biomarkers & Prevention, pp. 2965-2970 (2014).

Greenwald et al., "The B7 Family Revisited," Annu. Rev. Immunol., vol. 23, pp. 515-548 (2005).

Heine et al., "Successful treatment of refractory leiomyosarcoma with the PD-1 inhibitor nivolumab," Annals of Oneology Advance Access, 2 pages (Jul. 2016).

Huang et al., "The prognostic significance of PD-L1 in bladder cancer," Oncology Reports, vol. 33, pp. 3075-3084 (2015).

HuGEMM™ and HuCELL™ Models, "FactSheet," CrownBio, 8 pages (Oct. 2016).

International Search Report and Written Opinion dated Feb. 2, 2014 in International Application No. PCT/CN2014/091090 (English Translation).

Iwai et al., "Involvement of PD-L1 on tumor cells in the escape from host immune system and tumor immunotherapy by PD-L1 blockade," PNAS, vol. 99, No. 19, pp. 12293-12297 (Sep. 2002).

Jochems et al., "A combination trial of vaccine plus ipilimumab in metastatic castration-resistant prostate cancer patients: immune correlates," Cancer Immunol Immunother, vol. 63, pp. 407-418 (2014).

Keir et al., "PD-1 and its Ligands in Tolerance and Immunity," Annu. Rev. Immunol., vol. 26, pp. 677-704 (2008).

Klimka et al., "Human anti-CD30 recombinant antibodies by guided phage antibody selection using cell panning," British Journal of Cancer, vol. 83, No. 2, pp. 252-260 (2000).

Komiyama et al., "IL-17 Plays an Important Role in the Development of Experimental Autoimmune Encephalomyelitis," J. Immunol., vol. 177, pp. 566-573 (Jul. 2006).

Langer, C. J., "Emerging Immunotherapies in the Treatment of Non-Small Cell Lung Cancer (NSCLC)," American Journal of Clinical Oncology, pp. 1-9 (2014).

Latchman et al., "PD-L2 is a second ligand for PD-1 and inhibits T cell activation," Nat. Immunol., vol. 2, No. 3, pp. 261-268 (Mar. 2001).

Lazar-Molnar et al., "Crystal structure of the complex between programmed death-I (PD-1) and its ligand PD-L2," PNAS, vol. 105, No. 30, pp. 10483-10488 (Jul. 2008).

Li et al., "A Mini-Review for Cancer Immunotherapy: Molecular Understanding of PD-1/PD-L1 Pathway & Translational Blockade of Immune Checkpoints," Int. J. Mol. Soc., vol. 17, No. 1151, 22 pages (2016).

Li et al., "Analysis of Receptor Tyrosine Kinase Internalization Using Flow Cytometry," Methods Mol. Biol., vol. 457, pp. 305-317 (2008).

Lin et al., "The PD-1/PD-L1 complex resembles the antigen-binding Fv domains of antibodies and T cell receptors," PNAS, vol. 105, No. 8, pp. 3011-3016 (Feb. 2008).

Lipson et al., "From Discovery to Development: Blocking PD-1 and its Ligands," The Melanoma Letter, A Publication of the Skin Cancer Foundation, vol. 31, 6 pages (Summer 2013).

Mahoney et al., "The Next Immune-Checkpoint Inhibitors:PD-1/PD-L1 Blockade in Melanoma," Clin. Therapeutics, vol. 37, No. 4, pp. 761-782 (Nov. 2015).

Mamalis et al., "Targeting the PD-1 pathway: a promising future for the treatment of melanoma," Arch. Dermatol. Res.,vol. 306, pp. 511-519 (2014).

Nishimura et al., "Autoimmune Dilated Cardiomyopathy in PD-1 Receptor-Deficient Mice," Science, vol. 291, pp. 319-322 (Jan. 2001).

Nishimura et al., "Development of Lupus-like Autoimmune Diseases by Disruption of the PD-1 Gene Encoding an ITIM Motif-Carrying Immunoreceptor," Immunity, vol. 11, pp. 141-151 (Aug. 1999).

Nishimura et al., "PD-1: an inhibitory immunoreceptor involved in peripheral tolerance," Trends in Immunology, vol. 22, No. 5, pp. 265-268 (May 2001).

Okazaki et al., "A rheostat for immune responses: the unique properties of PD-1 and their advantages for clinical application," Nature Immunology, vol. 14, No. 12, pp. 1212-1218 (Dec. 2013).

Okazaki et al., "The PD-1-PD-L pathway in immunological tolerance," Trends Immunol., vol. 4, pp. 195-201 (Apr. 2006).

Panka et al., "Variable region framework differences result in decreased or increased affinity of variant anti-digoxin antibodies." Proc. Natl. Acad. Sci. USA, vol. 85, pp. 3080-3084 (1988).

Pardoll, D. M., "The blockade of immune checkpoints in cancer immunotherapy," Nature, vol. 12, pp. 252-264 (Apr. 2012).

Parry et al., "CTLA-4 and PD-1 Receptors Inhibit T-Cell Activation by Distinct Mechanisms," Mol. Cell. Biol., vol. 25, No. 21, pp. 9543-9553 (Nov. 2005).

Pascolutti et al., "Structure and Dynamics of PD-L1 and an Ultra-High-Affinity PD-1 Receptor Mutant," Structure, vol. 24, pp. 1719-1728 (Oct. 2016).

Paydas, S. "Pulmonary sarcoidosis induced by the anti-PD-1 monoclonal antibody pembrolizumab or post-immunotherapy granulomatous reaction: which is more appropriate terminology?" Annals of Oncology Advance Access, 4 pages (May 2016).

Postow et al., "Immune Checkpoint Blockade in Cancer Therapy," J. Clinical Oncology, vol. 33, No. 17, pp. 1974-1982 (Jun. 2015).

Press Release Archive, "Boehringer Ingelheim and Yale University collaborate to investigate novel immunotherapy targets across several therapeutic areas," Boehringer Ingelheim, 2 pages (Jan. 13, 2015).

Rader et al., "A phage display approach for rapid antibody humanization; Designed combinational V gene libraries," Proc. Natl. Acad. Sci., vol. 95, pp. 8910-8915 (Jul. 1998).

Rothermundt et al., "Successful treatment with an anti-PD-1 antibody for progressing brain metastases in renal cell cancer," Annals of Oncology, vol. 27, pp. 544-552 (2016).

Rudikoff et al., "Single amino acid substitution altering antigen-binding specificity," Proc. Natl. Acad. Sci, vol. 79, pp. 1979-1983 (Mar. 1982).

Sabatier et al., "Prognostic and predictive value of PDL1 expression in breast cancer," Oncotarget, vol. 6, No. 7, pp. 5449-5464 (Mar. 2015).

Sharpe et al., "The function of programmed cell death 1 and its ligands in regulating autoimmunity and infection," Nat. Immunol., vol. 8, No. 3, pp. 239-245 (Mar. 2007).

Sharpe et al., "The B7-CD28 Superfamily," Nature Reviews, vol. 2, pp. 116-126 (Feb. 2002).

Shindo et al., "Combination Immunotherapy with 4-IBB Activation and PD-1 Blockade Enhances Antitumor Efficacy in a Mouse Model of Subcutaneous Tumor," Anticancer Research, vol. 35, pp. 129-136 (2015).

Stadler et al., "New therapeutic options for advanced non-resectable malignant melanoma," Advances in Medical Sciences, vol. 60, pp. 83-88 (2015).

Storz, "Intellectual property issues of immune checkpoint inhibitors," mAbs, Jan. 2016, vol. 8, No. 1, pp. 10-26 (Jan. 2016).

Wang et al., "The prognostic value of PD-L1 expression for non-small cell lung cancer patients: A meta-analysis," Eur. J. Surg. Oncol., vol. 41, pp. 450-456 (2015).

Wang et al., "Modification of sPD1 with CRT induces potent anti-tumor immune responses in vitro and in vivo," Biomedicine & Pharmacotherapy, vol. 76, pp. 57-64 (2015).

Wang et al., "Molecular Modeling and Functional Mapping of B7-H1 and B7-DC Uncouple Costimulatory Function from PD-1 Interaction," J. Exp. Med., vol. 197, No. 3, pp. 1083-1091 (Apr. 2013).

Wei et al., "Strength of PD-1 signaling differentially affects T-cell effector functions," PNAS, pp. E2480-E2489 (Apr. 2013).

Wells et al., "Reaching for high-hanging fruit in drug discovery at protein-protein interfaces," Nature, vol. 450, pp. 1001-1009 (Dec. 2007).

(56) References Cited

OTHER PUBLICATIONS www.medscape.com [online]. "The 'Family Business' Behind the Flurry of PD-1 Inhibitors," Sep. 10, 2014. [Retrieved on Jan. 29, 2015]. Retrieved from the Internet: URL<http://www.medscape.com/viewarticle/831448_print>, 3 pages.

Xu et al., "Diversity in the CDR3 Region of VH is Sufficient for Most Antibody Specificities," Immunity, vol. 13, pp. 37-45 (Jul. 2000).

Zak et al., "Structure of the Complex of Human Programmed Death 1, PD-1, and its Ligand PD-L1," Structure, vol. 23, pp. 2341-2348 (Dec. 2015).

Zhan et al., "From monoclonal antibodies to small molecules: the development of inhibitors targeting the PD-1/PD-L1 pathway," Drug Discovery Today, 10 pages (Apr. 2016).

Zhang et al., "Structural and Functional Analysis of the Costimulatory Receptor Programmed Death-1," Immunity, vol. 20, pp. 337-347 (Mar. 2004).

\* cited by examiner

PD-1 ANTIBODY, ANTIGEN-BINDING FRAGMENT THEREOF, AND MEDICAL APPLICATION THEREOF

CROSS-REFERENCE TO RELATED APPLICATION

This application is a Continuation of co-pending U.S. patent application Ser. No. 15/103,758, filed Jun. 10, 2016, now U.S. Pat. No. 10,344,090 B2, issued Jul. 9, 2019, which was a Section 371 of International Application No. PCT/CN2014/091090, filed Nov. 14, 2014, which was published in the Chinese language on Jun. 18, 2015, under International Publication No. WO 2015/085847 A1, which claims priority under 35 U.S.C. § 119(b) to Chinese Application No. 2013-10681942.6, filed Dec. 12, 2013, the disclosures of which are incorporated herein by reference in their entirety.

FIELD OF THE INVENTION

The present invention relates to a PD-1 antibody, a PD-1 antigen-binding fragment, a chimeric antibody and humanized antibodies comprising the CDR of the PD-1 antibody, as well as a pharmaceutical composition comprising the PD-1 antibody and the antigen-binding fragment thereof, as well as its use as an anti-cancer drug.

BACKGROUND OF THE INVENTION

Tumor immunotherapy is a hot spot in tumor therapeutic area for a long time, T cell associated cancer immunotherapy is at the core position. Tumor immunotherapy affects tumors by fully utilizing and mobilizing cytotoxic T lymphocytes in patients with tumors; it may be the most effective and safest way for cancer treatment. At the same time, tumor escape is a huge obstacle faced by tumor immunotherapy, in which cancer cells promote rapid growth of the tumor via its inhibitory effect on the immune system.

There is extremely complex relationship between tumor immune escape mechanism and body's immune response to tumors. In early stage of tumor immunotherapy, tumor-specific killer T cells have biological activity, but lose the killing function in the late stage of tumor growth. So tumor immunotherapy is to utmostly enhance the response of the patient's own immune system to the tumor. The key of tumor immunotherapy is not only to activate the response of the existing immune system, but also to maintain the duration and intensity of the response of the immune system.

Human T-cell activation in vivo is implemented by a two-signaling-pathway system which not only needs to submit a MHC-antigen peptide via antigen-presenting cells to T cells to provide a first signal, but also requires a series of costimulatory molecules to provide a second signal, and then T cells exhibit normal immune response. This double-signaling system plays a vital role in balance of the immune system, and strictly regulates the different immune responses stimulated by endogenous and exogenous antigens. The absence of a second signal provided by co-stimulatory molecules will result in no response or sustained-specific T cell immune response, consequently leading to tolerance. Therefore, the second signal pathway plays a key regulatory role in the whole process of the immune response.

Programmed death-1 (PD-1), found in 1992, is a protein receptor expressed in T cell surface, and is involved in cell apoptosis. PD-1 belongs to CD28 family, exhibits 23% homology in amino acid sequence with cytotoxic T lymphocyte antigen 4 (CTLA-4), but is mainly expressed in activated T cells, B cells and myeloid cells, which is different from CTLA. PD-1 has two ligands, PD-L1 and PD-L2 respectively. PD-L1 is mainly expressed in T cells, B cells, macrophages, and dendritic cells (DC), and the expression is upregulated in the activated cells. The expression of PD-L2 is mainly limited to antigen-presenting cells, such as activated macrophages and dendritic cells.

New studies have detected high expression of PD-L1 protein in human tumor tissues such as breast cancer, lung cancer, stomach cancer, intestinal cancer, renal cancer, melanoma and others, and the expression levels of PD-L1 is closely related to clinical condition and prognosis of patients. For PD-L1 inhibits T cell proliferation through the second signaling pathway, blocking the binding of PD-L1/PD-1 becomes a very promising target in tumor immunotherapy field.

Currently, there are several multinational pharmaceutical companies engaged in monoclonal antibodies against PD-1, which maximize the self immune response of patients against tumor by blocking the binding of PD-L1/PD-1, and sequentially achieve the killing purpose against tumor cells, such as WO2009114335. In the clinical results of BMS' and Merck's PD-1 monoclonal antibodies, certain response rate have been observed in non-small cell lung cancer, melanoma and renal carcinoma, and the response rate exhibited prominently high relevance with PD-L1 expression in tumors, which suggested that PD-1 antibody exerts a positive effect on tumors.

The present invention provides a PD-1 antibody with high affinity, high selectivity, and high biological activity.

SUMMARY OF THE INVENTION

The present invention provides a PD-1 antibody or an antigen-binding fragment thereof, comprising:

a light chain variable region comprising at least one LCDR selected from those sequences as shown in: SEQ ID NO: 6, SEQ ID NO: 7 or SEQ ID NO: 8; and a heavy chain variable region comprising at least one HCDR selected from those sequences as shown in: SEQ ID NO: 3, SEQ ID NO: 4 or SEQ ID NO: 5.

In a preferred embodiment of the present invention, provided is a PD-1 antibody or an antigen-binding fragment thereof, wherein the light chain variable region comprises a LCDR1 as shown in SEQ ID NO: 6.

In a preferred embodiment of the present invention, provided is a PD-1 antibody or an antigen-binding fragment thereof, wherein the light chain variable region comprises a LCDR2 as shown in SEQ ID NO: 7.

In a preferred embodiment of the present invention, provided is a PD-1 antibody or an antigen-binding fragment thereof, wherein the light chain variable region comprises a LCDR3 as shown in SEQ ID NO: 8.

In a preferred embodiment of the present invention, provided is a PD-1 antibody or an antigen-binding fragment thereof, wherein the heavy chain variable region comprises a HCDR1 as shown in SEQ ID NO: 3.

In a preferred embodiment of the present invention, provided is a PD-1 antibody or an antigen-binding fragment thereof, wherein the heavy chain variable region comprises a HCDR2 as shown in SEQ ID NO: 4.

In a preferred embodiment of the present invention, provided is a PD-1 antibody or an antigen-binding fragment thereof, wherein the heavy chain variable region comprises a HCDR3 as shown in SEQ ID NO: 5.

In a preferred embodiment of the present invention, provided is a PD-1 antibody or an antigen-binding fragment thereof, wherein the light chain variable region comprises a LCDR1, a LCDR2 and a LCDR3 as shown in SEQ ID NO: 6, SEQ ID NO: 7 and SEQ ID NO: 8, respectively.

In a preferred embodiment of the present invention, provided is a PD-1 antibody or an antigen-binding fragment thereof, wherein the heavy chain variable region comprises a HCDR1, a HCDR2 and a HCDR3 as shown in SEQ ID NO: 3, SEQ ID NO: 4 and SEQ ID NO: 5, respectively.

In a preferred embodiment of the present invention, provided is a PD-1 antibody or an antigen-binding fragment thereof, wherein the light chain variable region comprises a LCDR1, a LCDR2 and a LCDR3 as shown in SEQ ID NO: 6, SEQ ID NO: 7 and SEQ ID NO: 8, respectively; and wherein the heavy chain variable region comprises a HCDR1, a HCDR2 and a HCDR3 as shown in SEQ ID NO: 3, SEQ ID NO: 4 and SEQ ID NO: 5, respectively.

In a preferred embodiment of the present invention, according to the PD-1 antibody or the antigen-binding fragment thereof provided herein, the antibody is a murine antibody or a fragment thereof.

In a preferred embodiment of the present invention, according to the murine antibody or the fragment thereof provided herein, the light chain variable region further comprises the light chain FR of murine κ, λ chain or a variant thereof.

In a preferred embodiment of the present invention, the murine antibody or the fragment thereof provided herein further comprises a light chain constant region of murine κ, λ chain or a variant thereof.

In a preferred embodiment of the present invention, according to the murine antibody or the fragment thereof provided herein, the heavy chain variable region further comprises the heavy chain FR of murine IgG1, IgG2, IgG3, IgG4 or a variant thereof.

In a preferred embodiment of the present invention, the murine antibody or the fragment thereof provided herein further comprises a heavy chain constant region of murine IgG1, IgG2, IgG3, IgG4 or a variant thereof.

In a preferred embodiment of the present invention, according to the PD-1 antibody or antigen-binding fragment provided herein, the antibody is a chimeric antibody or a fragment thereof.

In a preferred embodiment of the present invention, according to the PD-1 chimeric antibody or the fragment thereof provided herein, the light chain variable region sequence of the chimeric antibody is SEQ ID NO: 10.

In a preferred embodiment of the present invention, according to the PD-1 chimeric antibody or the fragment thereof provided herein, the heavy chain variable region sequence of chimeric antibody is SEQ ID NO: 9.

In a preferred embodiment of the present invention, the PD-1 chimeric antibody or the fragment thereof provided herein further comprises a light chain constant region of human κ, λ chain or a variant thereof.

In a preferred embodiment of the present invention, the PD-1 chimeric antibody or the fragment thereof provided herein further comprises a heavy chain constant region of human IgG1, IgG2, IgG3 or IgG4 or a variant thereof, preferably comprises a heavy chain constant region of human IgG2 or IgG4, or that of IgG1 which has no ADCC (antibody-dependent cell-mediated cytotoxicity) after amino acid mutation.

In a preferred embodiment of the present invention, according to the PD-1 antibody or the antigen-binding fragment provided herein, the antibody is a humanized antibody or a fragment thereof.

In a preferred embodiment of the present invention, according to the PD-1 humanized antibody or the fragment thereof provided herein, the light chain variable region of the humanized antibody further comprises light chain FR of human κ, λ chain or a variant thereof.

In a preferred embodiment of the present invention, according to the PD-1 humanized antibody or the fragment thereof provided herein, the light chain FR sequence of the light chain variable region of the humanized antibody is derived from a combination sequence of human germline light chains IGKV1-39 and JK4 as shown in SEQ ID NO: 14, comprising FR1, FR2 and FR3 of IGKV1-39 and FR4 of JK4.

In a preferred embodiment of the present invention, according to the PD-1 humanized antibody or the fragment thereof provided herein, the sequence of the humanized antibody light chain is shown in SEQ ID NO: 12 or a variant thereof.

In a preferred embodiment of the present invention, according to the PD-1 humanized antibody or the fragment thereof provided herein, the variant of humanized antibody light chain variable region comprises a 0-10 amino acid mutation in the light chain variable region, preferably A43S.

In a preferred embodiment of the present invention, the PD-1 humanized antibody or the fragment thereof provided herein further comprises a light chain constant region of human κ, λ chain or a variant thereof.

In a preferred embodiment of the present invention, according to the PD-1 humanized antibody or the fragment thereof provided herein, the heavy chain variable region further comprises a heavy chain FR of human IgG1, IgG2, IgG3, IgG4, or a variant thereof.

In a preferred embodiment of the present invention, according to the PD-1 humanized antibody or fragment thereof provided herein, the heavy chain FR sequence of the heavy chain variable region of the humanized antibody is derived from a combination sequence of human germline heavy chains IgHV3-7 and JH6 as shown in SEQ ID NO: 13, comprising FR1, FR2 and FR3 of IgHV3-7 and FR4 of JH6.

In a preferred embodiment of the present invention, according to the PD-1 humanized antibody or the fragment thereof provided herein, the sequence of the humanized antibody heavy chain is shown in SEQ ID NO: 11 or a variant thereof, wherein the variant preferably comprises a 0-10 amino acid mutation in the heavy chain variable region, more preferably G44R.

In a preferred embodiment of the present invention, the PD-1 humanized antibody or the fragment thereof provided herein further comprises a heavy chain constant region of human IgG1, IgG2, IgG3 or IgG4 or a variant thereof, and preferably comprises a heavy chain constant region of human IgG2 or IgG4 which has no ADCC, or that of IgG1 which has no ADCC (antibody-dependent cell-mediated cytotoxicity) after amino acid mutation. The variant is preferably a heavy chain constant region mutation which causes ADCC attenuation or deficiency, and more preferably N297A, L234A, L235A of IgG1, IgG2/4 chimera, and F235E or L234A/E235A of IgG4.

In a preferred embodiment of the present invention, according to the PD-1 antibody or the antigen-binding fragment provided herein, the antigen-binding fragment is Fab, Fv, sFv or F(ab')$_2$.

The present invention further provides a DNA molecule encoding the PD-1 antibody or the antigen-binding fragment described above.

The present invention further provides an expression vector comprising the DNA molecule as described above.

The present invention further provides a host cell transformed with the expression vector as described above.

In a preferred embodiment of the present invention, according to the host cell provided herein, the host cell is bacteria, preferably *E. coli*.

In a preferred embodiment of the present invention, the host cell provided herein is yeast, preferably *Pichia pastoris*.

The present invention further provides a pharmaceutical composition which comprises the PD-1 antibody or the antigen-binding fragment thereof as described herein and a pharmaceutically acceptable excipient, diluent or carrier.

The present invention further provides use of the above PD-1 antibody or the antigen-binding fragment, or the pharmaceutical composition containing the same, in the preparation of a medicament for treatment of a PD-1 mediated disease or disorder; wherein the disease is preferably cancer, more preferably PD-L1-expressing cancer; and the cancer is preferably breast cancer, lung cancer, stomach cancer, intestinal cancer, renal cancer, melanoma, and most preferably non-small cell lung cancer, melanoma and renal cancer.

The present invention further provides a method for treating and preventing the PD-1 mediated disease or disorder, comprising administering to a subject in need thereof a therapeutically effective amount of the PD-1 antibody or the antigen-binding fragment thereof according to the invention, or the pharmaceutical composition comprising the same; wherein the disease is preferably cancer, more preferably PD-L1-expressing cancer; the cancer is preferably breast cancer, lung cancer, stomach cancer, intestinal cancer, renal cancer, melanoma, non-small cell lung cancer, and most preferably non-small cell lung cancer, melanoma and renal cancer.

DETAILED DESCRIPTION OF THE INVENTION

1. Definitions

Figure 1:
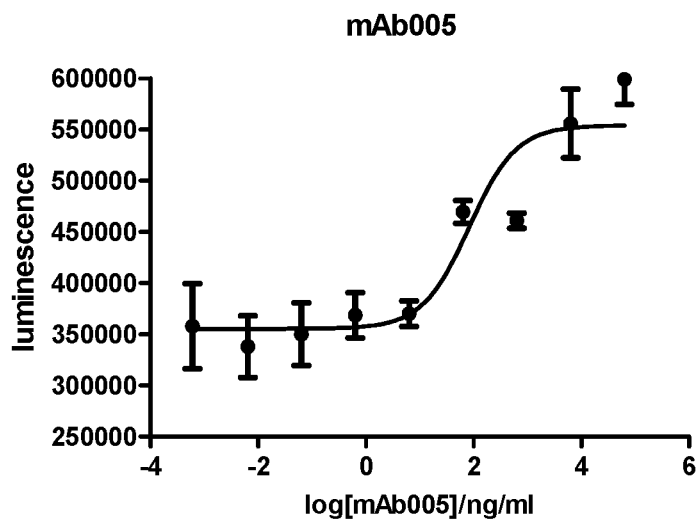
FIG. 1: Human peripheral blood mononuclear cell proliferation assay. Result shows that the test PD-1 antibody mAb005 can effectively stimulate the proliferation of human peripheral blood mononuclear cells, with EC50 of 83 ng/ml.

In order to more readily understood the invention, certain technical and scientific terms are specifically defined below. Unless specifically defined elsewhere in this document, all other technical and scientific terms used herein have the meaning commonly understood by one of ordinary skill in the art to which this invention belongs.

As used herein, the single-letter code and the three-letter code for amino acids are as described in J. biol. chem, 243, (1968) p 3558.

As used herein, "Antibody" refers to immunoglobulin, a four-peptide chain structure connected together by disulfide bonds between two identical heavy chains and two identical light chains. Different immunoglobulin heavy chain constant regions exhibit different amino acid compositions and rank orders, thereby presenting different kinds of antigenicity. Accordingly, immunoglobulins can be divided into five categories, or called immunoglobulin isotypes, namely IgM, IgD, IgG, IgA and IgE, their heavy chains are μ chain, δ chain, γ chain, a chain and E chain, respectively. According to its amino acid composition of hinge region and the number and location of heavy chain disulfide bonds, the same type of Ig can be divided into different sub-categories, for example, IgG can be divided into IgG1, IgG2, IgG3, and IgG4. Light chain can be divided into κ or λ chain considering of different constant regions. Each of the five Igs can have κ or λ chain.

In the present invention, the antibody light chain variable region mentioned herein further comprises a light chain constant region, which comprises a human or murine κ, λ chain or a variant thereof.

In the present invention, the antibody heavy chain variable region mentioned herein further comprises a heavy chain constant region, which comprises human or murine IgG1, 2, 3, 4 or a variant thereof.

Near the N-terminal sequence of the antibody heavy chains and light chains, about 110 amino acid sequence varies largely, known as the variable region (V region); the rest of the amino acid sequence near the C-terminus is relative stable, known as the constant region (C region). Variable region comprises three hypervariable regions (HVR) and four relatively conserved sequence framework region (FR). The three hypervariable regions determine the specificity of the antibody, also known as a complementarity determining region (CDR). Each light chain variable region (LCVR) and each heavy chain variable region (HCVR) is composed of three CDRs and four FRs, with sequentially order from the amino terminal to the carboxyl terminal being: FR1, CDR1, FR2, CDR2, FR3, CDR3, and FR4. Three light chain CDRs refer to LCDR1, LCDR2, and LCDR3; three heavy chain CDRs refer to HCDR1, HCDR2 and HCDR3. The numbers and locations of CDR amino acid residues in LCVR and HCVR of the antibody or the antigen-binding fragment herein correspond with known Kabat numbering criteria (LCDR1-3, HCDE2-3), or correspond with kabat and chothia numbering criteria (HCDR1).

The term "murine antibody" in the present invention refers to anti-human-PD-1 monoclonal antibody prepared according to the knowledge and skills in the art. During the preparation, a test object was injected with PD-1 antigen, and then hybridoma expressing antibody which possesses desired sequence or functional characteristics was separated. In a preferred embodiment of the present invention, the murine PD-1 antibody or the antigen-binding fragment thereof further comprises a light chain constant region of murine κ, λ chain or a variant thereof, or further comprises a heavy chain constant region of murine IgG1, IgG2, IgG3 or IgG4, or a variant thereof.

The term "chimeric antibody", is an antibody which is formed by fusing the variable region of a murine antibody with the constant region of a human antibody, the chimeric antibody can alleviate the murine antibody-induced immune response. To establish a chimeric antibody, hybridoma secreting specific murine monoclonal antibody is firstly established, a variable region gene is cloned from mouse hybridoma cells, then a constant region gene of a human antibody is cloned as desired, the mouse variable region gene is ligated with the human constant region gene to form a chimeric gene which can be inserted into a human vector, and finally the chimeric antibody molecule is expressed in the eukaryotic or prokaryotic industrial system. In a preferred embodiment of the present invention, the light chain variable region of PD-1 chimeric antibody further comprises the light chain FR of murine κ, λ chain or a variant thereof, and the sequence of the light chain variable region is shown in SEQ ID NO: 10. The heavy chain variable region of the PD-1 chimeric antibody further comprises the heave chain FR of murine IgG1, IgG2, IgG3, IgG4 or a variant thereof, and the sequence of the heavy chain variable region is shown in SEQ ID NO: 10. The constant region of a human antibody is selected from the heavy chain constant region of human IgG1, IgG2, IgG3 or IgG4 or a variant thereof, preferably comprises the heavy chain constant region of human IgG2 or IgG4, or that of IgG1 which has no ADCC (antibody-dependent cell-mediated cytotoxicity) after amino acid mutation.

The term "humanized antibody", also known as CDR-grafted antibody, refers to an antibody generated by grafting murine CDR sequences into a variable region framework of a human antibody, namely, a sequence of human germline antibody framework of different type. Humanized antibody overcomes the disadvantageously strong antibody response induced by the chimeric antibody which carries a large amount of murine protein components. Such framework sequences can be obtained from public DNA database covering germline antibody gene sequences or published references. For example, germline DNA sequences of human heavy and light chain variable region genes can be found in "VBase" human germline sequence database (available on web www.mrccpe.com.ac.uk/vbase), as well as can be found in Kabat, E A, et al, 1991 Sequences of Proteins of Immunological Interest, $5^{th}$ Ed. In a preferred embodiment of the invention, the murine CDR sequences of PD-1 humanized antibody are selected from SEQ ID NO: 3, 4, 5, 6, 7, 8. Human antibody variable region frameworks were designed and selected such that the light chain FR sequence of the antibody light chain variable region is derived from combination sequence of human germline light chains IGKV1-39 and JK4: SEQ ID NO: 14, comprising FR1, FR2 and FR3 of IGKV 1-39 and FR4 of JK4; the heavy chain FR sequence of the antibody heavy chain variable region is derived from combination sequence of human germline heavy chains IgHV3-7 and JH6: SEQ ID NO: 13, comprising FR1, FR2 and FR3 of IgHV3-7 and FR4 of JH6. To avoid activity decrease during immunogenicity reduction, the variable region of the human antibody is subjected to a minimum back mutation to maintain the activity.

As used herein, "antigen-binding fragment" refers to a Fab fragment, a Fab' fragment, a F(ab')2 fragment with antigen-binding activity, as well as a Fv fragment sFv fragment binding with human PD-1; comprising one or more CDR regions of antibodies described in the present invention selected from the group consist of SEQ ID NO:3 to SEQ ID NO:8. Fv fragment is a minimum antibody fragment comprising a heavy chain variable region, a light chain variable region, and all antigen-binding sites without a constant region. Generally, Fv antibody further comprises a polypeptide linker between the VH and VL domains, and is capable of forming a structure required for antigen binding. Also, different linkers can be used to connect the variable regions of two antibodies to form a polypeptide, named single chain antibody or single chain Fv (sFv). As used herein, the term "binding with PD-1", means interacting with human PD-1. As used herein, the term "antigenic determinant" of the present invention, refers to discontinuous three-dimensional sites on the antigen, recognized the antibody or the antigen-binding fragment of the present invention.

As used herein, the term "ADCC", namely antibody-dependent cell-mediated cytotoxicity, refers to cells expressing Fc receptors directly kill target cells coated by an antibody through recognizing the Fc segment of the antibody. ADCC effector function of the antibody can be reduced or eliminated via modification of the Fc segment in IgG. The modification refers to mutations of the antibody heavy chain constant region, such as mutations selected from N297A, L234A, L235A in IgG1; IgG2/4 chimera; F235E, or L234A/E235A mutations in IgG4.

As used herein, fusion protein described in the present invention is a protein product obtained by co-expressing two genes via recombinant DNA technology. Recombinant PD-1 extracellular domain Fc fusion protein obtained by co-expressing a PD-1 extracellular domain and a human antibody Fc fragment via recombinant DNA technology. The PD-1 extracellular domain refers to the moiety of PD-1 outside cytomembrane, the sequence of which is the scribing region of SEQ ID NO: 1 below.

Methods for producing and purifying antibodies and antigen-binding fragments are well known in the art and can be found, for example, in Antibody Experimental Technology Guide of Cold Spring Harbor, Chapter 5-8 and 15. For example, mice can be immunized with human PD-1, or fragments thereof, and the resulting antibodies can then be renatured, purified and sequenced using conventional methods well known in the art. Antigen-binding fragments can also be prepared by conventional methods. The antibody or the antigen-binding fragment of the present invention is genetically engineered to introduce one or more human framework regions (FRs) to a non-human derived CDR. Human FR germline sequences can be obtained from ImMunoGeneTics(IMGT) via their website http://imgt.cines.fr, or from The Immunoglobulin FactsBook, 2001ISBN012441351. Specifically, light chain FR germline for use in the antibody or the antigen-binding fragment of the present invention include A3 and 02. Particular heavy chain FR germline for use in the antibody or the antigen-binding fragment of the present invention include VH3-21 and VH3-23.

The engineered antibody or antigen-binding fragment of the present invention may be prepared and purified using conventional methods. For example, cDNA sequences encoding a heavy chain (SEQ ID NO: 11) and a light chain (SEQ ID NO: 12) may be cloned and recombined into a GS expression vector. The recombined immunoglobulin expression vector may then stably transfect CHO cells. As a more recommended method well known in the art, mammalian expression of antibodies will result in glycosylation, typically at the highly conserved N-terminal in the FC region. Stable clones may be obtained through expression of an antibody specifically binding to human PCSK9. Positive clones may be expanded in a serum-free culture medium for antibody production in bioreactors. Culture medium, into which an antibody has been secreted, may be purified by conventional techniques. For example, the medium may be conveniently applied to a Protein A or G SEPHAROSE® FF column that has been equilibrated with a compatible buffer. The column is washed to remove nonspecific binding components. The bound antibody is eluted by PH gradient and antibody fragments are detected by SDS-PAGE, and then pooled. The antibody may be filtered and concentrated using common techniques. Soluble aggregate and multimers may be effectively removed by common techniques, including size exclusion or ion exchange. The obtained product may be immediately frozen, for example at −70° C., or may be lyophilized.

The antibody of the present invention is a monoclonal antibody. Monoclonal antibody or mAb, as used herein, refers to an antibody that is derived from a single clone including but not limited to any eukaryotic, prokaryotic, or phage clone. Monoclonal antibodies and antigen-binding fragments thereof can be recombined, for example, by hybridoma technologies, recombinant technologies, phage display technologies, synthetic technologies (e.g., CDR-grafting), or other technologies known in the art.

"Administration" and "treatment," as it applies to an animal, human, experimental subject, cell, tissue, organ, or biological fluid, refers to contacting an exogenous pharmaceutical, therapeutic, diagnostic agent, or composition with the animal, human, subject, cell, tissue, organ, or biological fluid. "Administration" and "treatment" can refer, e.g., to therapeutic, pharmacokinetic, diagnostic, research, and experimental methods. Treatment of a cell encompasses contacting a reagent with the cell, as well as contacting a reagent with a fluid, where the fluid is in contact with the cell. "Administration" and "treatment" also means in vitro and ex vivo treatments, e.g., of a cell, by a reagent, diagnostic, binding compound, or by another cell. "Treatment," as it applies to a human, veterinary, or a research subject, refers to therapeutic treatment, prophylactic or preventative measures, to research and diagnostic applications.

"Treat" means to administer a therapeutic agent, such as a composition comprising any of the binding compounds of the present invention, internally or externally to a patient having one or more disease symptoms for which the agent has known therapeutic activity. Typically, the agent is administered in an amount effective to alleviate one or more disease symptoms in the treated patient or population, whether by inducing the regression of or inhibiting the progression of such symptom(s) to any clinically measurable degree. The amount of a therapeutic agent that is effective to alleviate any particular disease symptom (also referred to "therapeutically effective amount") may vary according to factors such as the disease state, age, and weight of the patient, and the ability of the drug to elicit a desired response in the patient. Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the disease symptom(s) of interest in every patient, it should alleviate the target disease symptom(s) of interest in a statistically significant number of patients as determined by any statistical test known in the art such as the Student's t-test, the chi-square test, the U-test according to Mann and Whitney, the Kruskal-Wallis test (H-test), Jonckheere-Terpstra-test and the Wilcoxon-test.

"Conservative modifications" or "conservative replacement or substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 ($4^{th}$ Ed.)). In addition, substitutions of structurally or functionally similar amino acids are less likely to disrupt biological activity.

"Consisting essentially of," or its variation as used throughout the specification and claims, indicate the inclusion of any recited elements or group of elements, and the optional inclusion of other elements of similar or different nature than the recited elements, which do not materially change the basic or novel properties of the specified dosage regimen, method, or composition. As a nonlimiting example, a binding compound which consists essentially of a recited amino acid sequence may also include one or more amino acids that do not materially affect the properties of the binding compound.

"Effective amount" encompasses an amount sufficient to ameliorate or prevent a symptom or sign of a medical condition. Effective amount also means an amount sufficient to allow or facilitate diagnosis. An effective amount for a particular patient or veterinary subject may vary depending on factors such as the condition being treated, the general health of the patient, the route and dose of administration and the severity of side affects. An effective amount can be the maximal dose or dosing protocol that avoids significant side effects or toxic effects.

"Exogenous" refers to substances that are produced outside an organism, cell, or human body, depending on the context. "Endogenous" refers to substances that are produced within a cell, organism, or human body, depending on the context.

"Homology" refers to sequence similarity between two polynucleotide sequences or between two polypeptides. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10 positions in two sequences are matched or homologous when the sequences are optimally aligned, then the two sequences are 60% homologous. Generally, the comparison is made when two sequences are aligned to give maximum percent homology.

As used herein, the expressions "cell," "cell line," and "cell culture" are used interchangeably and all such designations include progeny. Thus, the words "transformants" and "transformed cells" include the primary subject cell and cultures derived therefrom without considering the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific moiety of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to corresponding strands of the template to be amplified. The 5' terminal nucleotides of the two primers can be identical with the ends of the material to be amplified. PCR can be used to amplify specific RNA sequences, specific DNA sequences from total genomic DNA, and cDNA transcribed from total cellular RNA, bacteriophage or plasmid sequences, etc. See generally Mullis et al. (1987) Cold Spring Harbor Symp. Ouant. Biol. 51:263; Erlich, ed., (1989) PCR TECHNOLOGY (Stockton Press, N.Y.). As used herein, PCR is considered as one, but not the only, example of a nucleic acid polymerase reaction method for amplifying a nucleic acid test sample, comprising the use of a known nucleic acid as a primer and a nucleic acid polymerase to amplify or generate a specific moiety of the nucleic acid.

"Optional" or "optionally" means that the event or situation that follows may but does not necessarily occur, and the description includes the instances in which the event or circumstance does or does not occur. For example, "optionally comprises 1-3 antibody heavy chain variable regions" means the antibody heavy chain variable region with specific sequence can be, but not necessarily be present.

"Pharmaceutical composition" refers to one containing a mixture of one or more compounds according to the present invention or a physiologically/pharmaceutically acceptable salt or produg thereof with other chemical components, as well as additional components such as physiologically/pharmaceutically acceptable carriers and excipients. The pharmaceutical composition aims at promoting the administration to an organism, facilitating the absorption of the active ingredient and thereby exerting a biological effect.

DETAILED DESCRIPTION OF THE INVENTION

Hereinafter, the present invention is further described with reference to examples; however, the scope of the present invention is not limited thereto. In the examples of the present invention, where specific conditions are not described, the experiments are generally conducted under conventional conditions as described in Antibody Technology Laboratory Manual and Mecular Cloning Manual of Cold Spring Harbor, or under conditions proposed by the material or product manufacturers. Where the source of the reagents is not specifically given, the reagents are commercially available conventional reagents.

Example 1: Antibody Preparation

Murine monoclonal antibodies against human PD-1 were generated. Purified recombinant PD-1 extracellular domain Fc fusion protein (PD-1 Fc) (SEQID NO: 1); or CHO cells transfected with PD-1 (SEQ ID NO: 2) was used as an antigen to immunize Balb/C mice and SJL mice. Human PD-1 antigen was purchased from ORIGENE, Cat No. SC117011, NCBI Reference Sequence: NM_005018.1.

```
PD-1 Fc, recombinant PD-1 extracellular domain Fc
fusion protein (SEQ ID NO: 1):
MDMRVPAQLLGLLLLWFPGSRCPGWFLDSPDRPWNPPTFSPALLVVTEGD

NATFTCSFSNTSESFVLNWYRMSPSNQTDKLAAFPEDRSQPGQDCRFRVT

QLPNGRDPHMSVVRARRNDSGTYLCGAISLAPKAQIKESLRAELRVTERR

AEVPTAHPSPSPRPAGQFQTLVDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK.

PD-1, PD-1 antigen transfecting cells
(SEQ ID NO: 2):
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQFQTLVVGVVGGLLGSLVLLVWVLAVICSRAARGTI

GARRTGQPLKEDPSAVPVFSVDYGELDFQWREKTPEPPVPCVPEQTEYAT

IVFPSGMGTSSPARRGSADGPRSAQPLRPEDGHCSWPL.
```

Immunization with the PD-1 extracellular domain-Fc fusion protein is divided into high dose (50 ug) and low dose (10 ug) of the purified antigen, immunization with the PD-1 transfected CHO cells uses $0.5-1 \times 10^7$ cells. Immunization was carried out on day 0, 14, and 35 respectively with Complete Freund's adjuvant; blood was sampled in the retro-orbital site to monitor the immune response. Mice with anti-PD-1 human immunoglobulin titer were obtained by plasma screening ELISA. On day 56, mice with the highest anti-PD-1 human immunoglobulin titer were subjected to boost immunization. 3 days later, mice were sacrificed and the spleen was removed for fusion. Hybridoma fusions were screened and a murine monoclonal antibody mAb005 was obtained. The heavy chain variable region sequence and light chain variable region sequence of the murine monoclonal antibody mAb005 are as follows:

```
mAb005 HCVR
                                         SEQ ID NO: 9
EVLMVESGGGLVKPGGSLKLSCAASGFTFSSYMMSWVRQTPEKRLEWVAT

ISGGGANTYYPDSVKGRFTISRDNAKNTLYLQMSSLRSEDTALYYCARQL

YYFDYWGQGTTLTVSS mAb005 LCVR
                                        SEQ ID NO: 10
DIQMTQSPASQSASLEGEGVTITCLASQTIGTWLTWYQQKPGKSPQLLIY

TATSLADGVPSRFSGSGSGTKFSFKISSLQAEDFVTYYCQQVYSIPWTFG

GGTKLEIK
```

CDR sequences are as follows:

| Name | Sequence | Numbering |
|---|---|---|
| HCDR1 | SYMMS | SEQ ID NO: 3 |
| HCDR2 | TISGGGANTYYPDSVKG | SEQ ID NO: 4 |
| HCDR3 | QLYYFDY | SEQ ID NO: 5 |
| LCDR1 | LASQTIGTWLT | SEQ ID NO: 6 |
| LCDR2 | TATSLAD | SEQ ID NO: 7 |
| LCDR3 | QQVYSIPWT | SEQ ID NO: 8 |

Example 2: Antibody Screening

In vitro PD-1 antibody ELISA binding assay:

The PD-1 antibody blocks signaling pathway of PD-1 and its ligand by binding to PD-1 extracellular domain. In vitro ELISA assay is used to detect the binding property of the PD-1 antibody. Biotinylated PD-1 extracellular domain FC fusion protein (PD-1 FC) is coated onto 96-well plates by binding to neutralization avidin. Signal intensity after the addition of the antibody is used to determine the binding property of the antibody and PD-1.

Neutralization avidin (binding to biotin) was diluted to 1 μl/ml with PBS buffer, pipetted into a 96-well plate with at 100 μl/well and standed for 16 h-20 h at 4° C. The 96-well plate was washed once with PBST (PH7.4 PBS, containing 0.05% tweeen20) after PBS buffer was removed, then the plate was incubated and blocked for 1 h at room temperature with addition of 120 μl/well PBST/1% milk. After removal of the blocking solution, the plate was washed with PBST buffer, followed by addition of 1 μg/ml biotin-labeled PD1-FC which was diluted by PBST/1% milk, and incubated for 1 h at room temperature. After removal of the blocking solution, the plate was washed with PBST buffer for 3 times, followed by addition of the test PD-1 antibody which was diluted to a suitable concentration by PBST/1% milk, and incubated for 1.5 h at room temperature. After removal of reaction system, the plate was washed for 3 times with PBST buffer, followed by addition of 100 μl/well HRP-labeled anti-murine secondary antibody (The Jackson Laboratory) which was diluted by PBST/1% milk, and incubated for 1 h at room temperature. After being washed with PBST for three times, the plate was added with 100 μl/well TMB, and incubated for 5-10 min at room temperature. Then the reaction was terminated with addition of 100 μl/well 1M $H_2SO_4$. The absorbance value at 450 nm was read on NOVOStar microplate reader; the ELISA binding $EC_{50}$ value was calculated.

| Test Antibody | ELISA, EC50, nM | |
| --- | --- | --- |
| | human PD-1 | cyno PD-1 |
| mAb005 | 0.25 | 0.27 |

The results demonstrated that the antibody mAb005 showed excellent binding activity to human PD-1Fc (human PD-1) and cynomolgus PD-1Fc (cyno PD-1).

In vitro blocking assay of binding of PD-1 antibody and PD-1 ligand:

PD-L1 on the surface of a tumor cell exhibits suppressive effect on the proliferation of T cells by binding to PD-1 on the surface of a T cell. The PD-1 antibody blocks PD-L1/PD-1 signaling pathway by binding to PD-1 so as to stimulate T cell proliferation. PD-1/PD-L1 binding blocking assay is used to detect the blocking activity of PD-1 antibody on the signaling pathway.

In this experiment, a 96-well plate was coated with a PD-1 protein with the extracellular domain fused with FC (PD-1-FC), and incubated with the test PD-1 antibody; later biotin-labeled PD-L1 was added for incubation. After washing the plate, the binding amount of biotin-labeled PD-L1 was detected; the blocking $IC_{50}$ value of PD-1 antibody for ligand PD-L1 binding was calculated.

PD-1-FC was diluted to 1 μg/ml with PH 9.6 CB buffer (1.59 g $Na_2CO_3$ and 2.93 g $NaHCO_3$ were dissolved in 1 L of distilled water), pipetted into a 96-well plate at 100 μl/well and standed for 16 h-20 h at 4° C. The 96-well plate was washed once with PBST (PH7.4 PBS, containing 0.05% tweeen20) after PBS buffer was removed, then the plate was incubated and blocked for 1 h at room temperature with 120 μl/well PBST/1% milk. After removal of the blocking solution, the plate was washed with PBST buffer once, followed by addition of 90 μl of test PD-1 antibody which was diluted to a suitable concentration with sample diluents (PH7.4 PBS containing 5% BSA, 0.05% Tween20), and incubated for 1 h at 4° C. Then 10 X concentrations of biotin-labeled PD-L1 (Beijing Sino Biological Inc.) (10 μg/ml) was added to the plate at 10 μl/well, oscillated and mixed by an oscillator, and incubated at 37° C. for 1 h. After removal of the reaction system, the plate was washed for 6 times with PBST buffer, followed by addition of 100 ul/well Streptavidin-Peroxidase Polymer which was diluted by PBST at a ratio of 1:400, and incubated under oscillation for 50 min at room temperature. After being washed with PBST for 6 times, the plate was added with 100 μl/well TMB, and incubated for 5-10 min at room temperature. Then the reaction was terminated with addition of 100 μl/well 1M $H_2SO_4$. The absorbance value at 450 nm was read on the NOVOStar microplate reader; the blocking $IC_{50}$ value of PD-1 for ligand PD-L1 binding was calculated.

| Test antibody | LBB assay IC50, nM |
| --- | --- |
| mAb005 | 1.13 |

The result showed that the antibody mAb005 was very effective to block the binding of PD-L1 with PD-1.

Example 3: Binding Selectivity Assay of PD-1 Antibody In Vitro

To detect the specific binding activity of PD-1 antibody to other proteins of the PD-1 family, human CTLA4 and human CD28 were used for binding assays. Meanwhile, the PD-1 of mice was also used for binding assays so as to determine the diversity of PD-1 antibody for different species other than human/monkey.

Selectively binding proteins: human PD-1, human ICOS, human CTLA4, human CD28 and mouse PD-1, (Beijing Sino Biological Inc.), were respectively diluted to 1 μg/ml with PBS buffer, pipetted into a 96-well plate at 100 μl/well and standed for 16 h-20 h at 4° C. The 96-well plate was washed once with PBST (PH7.4 PBS, containing 0.05% tweeen20) after PBS buffer was removed, then the plate was incubated and blocked for 1 h at room temperature with 120 μl/well PBST/1% milk. After removal of the blocking solution, the plate was washed with PBST buffer for 3 times, followed by addition of the test PD-1 antibody, and incubated for 1.5 h at room temperature. After removal of the reaction system, the plate was washed for 3 times with PBST, followed by addition of 100 μl/well HRP-labeled anti-murine secondary antibody (The Jackson Laboratory) which was diluted by PBST/1% milk, and incubated for 1 h at room temperature. The plate was washed for 3 times with PBST, followed by addition of 100 μl/well TMB, and incubated for 5-10 min at room temperature. Then the reaction was terminated with addition of 100 μl/well 1M $H_2SO_4$. The absorbance value at 450 nm was read on the NOVOStar microplate reader.

| Test Antibody | human PD1-FC | mouse PD1-Fc | human ICOS/Fc | human CTLA4 | human CD28 |
|---|---|---|---|---|---|
| mAb005 | 2.64 | 0.07 | 0.15 | 0.17 | 0.12 |

The result demonstrated that mAb005 antibody exhibites no specific binding activity to other proteins of the PD-1 family. Meanwhile, mAb has no species cross-reactivity against murine PD-1.

Example 4: In Vitro Cell Binding Assay of PD-1 Antibody

FACS (fluorescence-activated cell sorter) is a test method for detecting interaction of proteins and cells. The test is used for detecting the binding activity of PD-1 antibody to native PD-1 expressed on the cell surface. Cells used in the test are CHO cells highly expressing PD-1 (see Example 1, CHO cells transfected with PD-1 (SEQID NO: 2)).

The CHO cells highly expressing PD-1 were centrifuged at 1000 rpm for 5 minutes, and the pellet was collected and suspended with 10-15 ml of precooled flow buffer for cell count. Cells were centrifuged at 1000 rpm in 50 ml centrifuge tubes for 5 minutes and collected. After removal of the supernatant, the pellet was resuspended with precooled blocking buffer with density of $0.5$-$1.0 \times 10^7$ cells/ml. After incubation at 4° C. for 30 minutes, re-suspension was pipetted to the 96-well plate at 100 μl/well. The 96-well plate was centrifuged at 1500 rpm for 5 minutes, the supernatant was discarded. 100 μl of primary antibody was added to each well; the cells were resuspended, and incubated in the dark for 60 minutes at 4° C. After centrifugation and discard of the supernatant, 100 μl of FITC-labeled secondary antibody (BD Biosciences) diluted at 1:400 was added. The cells were resuspended and incubated in the dark for 60 minutes at 4° C. Cells were washed twice with flow buffer, resuspended and fixed with 1% paraformaldehyde for flow cytometry assay.

|  | MFI | | | |
|---|---|---|---|---|
| Test Antibody | 50 nM | 5 nM | 0.5 nM | 0.05 nM |
| mAb005 | 468 | 319 | 71.2 | 14 |

The results show that mAb005 antibody can also bind to PD-1 on the cell surface.

Example 5: In Vitro Binding Affinity and Kinetic Assay

BIACORE™ method is a recognized assay which objectively detects the interactional affinity and kinetics of proteins. We analyzed the characterized affinity and binding kinetics of the test PD-1 antibody of the present invention by BIACORE™ (GE).

According to the instruction of a kit provided by BIACORE™, the test PD-1 antibody of the present invention was covalently linked to CM5 (GE) chip using a standard amino coupling method. Then a series of gradient concentrations of PD-1 His protein (Beijing Sino Biological Inc.), which were diluted in the same buffer, were loaded into each cycle successively. After that, the samples were regenerated with regenerated reagent in the kit. The antigen-antibody binding kinetics was tracked for 3 minutes and the dissociation kinetics was tracked for 10 minutes. The data obtained was analyzed by GE's BIAevaluation software using 1:1 (Langmuir) binding model. Ka (kon), kd (koff) and KD values determined by the assay were shown in the following table.

| Test Antibody | ka (1/Ms) | kd (1/s) | KD (M) |
|---|---|---|---|
| mAb005 | 1.057E+5 | 3.769E−4 | 3.566E−9 |

The results showed that the binding Kd value of the antibody mAb005 to PD-1 reached to 3.57 nM.

Example 6: In Vitro Cytology Test

Fresh human peripheral blood mononuclear cells (PBMC) proliferation assay affected by antibody is used to detect the cell activity of the antibody mAb005.

Figure 2:
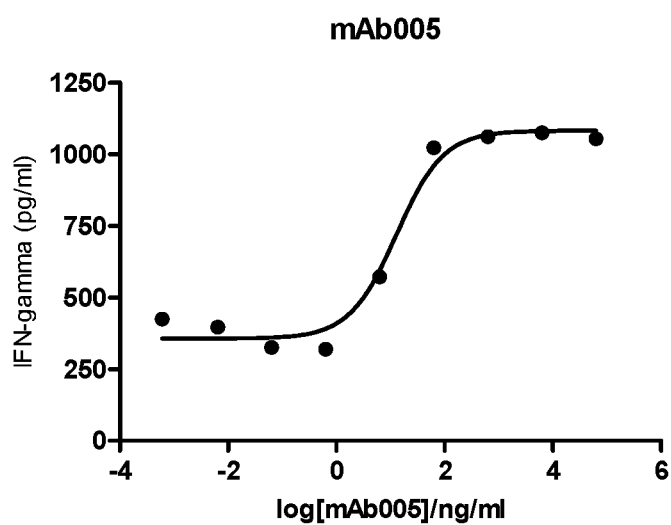
FIG. 2: Human peripheral blood mononuclear cell cytokine IFN-γ secretion test. Result shows that the test PD-1 antibody mAb005 can stimulate PBMC proliferation, and effectively stimulate secretion of cytokine IFN-γ at the same time, with EC50 of 13 ng/ml.

Fresh human PBMC density was adjusted to $2 \times 10^6$/ml, seeded in a 6-well plate at 2 ml/well, and incubated for 6 hours at 37° C., 5% $CO_2$. After the suspension cells were discarded, each well of adherent cells was mixed with 2 ml of RPMI1640 medium containing 100 ng/ml GM-CSF (granulocyte colony stimulating biological factor) and 100 ng/ml IL-4, and another 1 ml of RPMI1640 medium containing 100 ng/ml GM-CSF and 100 ng/ml IL-4 after incubation for 2 days, then the cells were continually cultured for 2 days, followed by addition of 100 ng/ml TNF-α (tumor necrosis factor-α) each well, and cultured for another 2 days to obtain mature dendritic cells. The dendritic cells and allogeneic T cells were respectively centrifugated and resuspended at a concentration of $1 \times 10^6$/ml and $1 \times 10^5$/ml, and pipetted into a 96-well plate at 100l/well, followed by addition of 20 μl/well of antibody which was diluted to different concentration gradients with PBS, and the cells were cultured in 37° C., 5% $CO_2$ incubator for 5 days. Thereafter, 100 μl of cell culture was sampled to detect the cell proliferation with CellTiter-Glo® Luminescent Cell Viability Assay kit. The result was shown in FIG. 1, indicating that the test PD-1 antibody mAb005 can effectively stimulate the proliferation of human peripheral blood mononuclear cells, with EC50 of 83 ng/ml. The remaining sample was detected for secretion of cytokine IFN-γ. The result was shown in FIG. 2, demonstrating that the test PD-1 antibody mAb005 could stimulate PBMC proliferation, and effectively stimulate secretion of cytokine IFN-γ at the same time, with EC50 of 13 ng/ml.

Example 7: Murine Antibody Humanization

With reference to the sequences of the light chain variable region (mAb005 LCVR, SEQ ID NO: 10) and the heavy chain variable region (mAb005 HCVR, SEQ ID NO: 9) of the mAb005 antibody, humanized templates best matching with their non-CDR in Germline database were selected. The antibody heavy chain template is IgHV3-7/JH6, selecting for FR1, FR2, FR3 of human germline light chain IGKV1-39 and FR4 of JK4, with sequence of SEQ ID NO: 13; light chain template is IGKV1-39/JK4, selecting for FR1, FR2, FR3 of human germline light chain IGKV1-39, and FR4 of JK4, with sequence of SEQ ID NO: 14.

Human germline heavy chain template
(SEQ ID NO: 13):
EVQLVESGGGLVQPGGSLRLSCAASGFTFSSYWMSWVRQAPGKGLEWVAN

IKQDGSEKYYVDSVKGRFTISRDNAKNSLYLQMNSLRAEDTAVYYCARWG

QGTTVTVSS;

Human germline light chain template
(SEQ ID NO: 14):
DIQMTQSPSSLSASVGDRVTITCRASQSISSYLNWYQQKPGKAPKLLIYA

ASSLQSGVPSRFSGSGSGTDFTLTISSLQPEDFATYYCFGGGTKVEIK.

The CDR of the murine antibody was grafted to the selected humanization template, replacing the CDR of human template, and then recombined with IgG4 constant region to obtain a humanized antibody H005-1. Afterwards, based on three-dimensional structure of the murine antibody, embedded residues, residues directly interacted with the CDR, and residues which significantly influence the conformation of VL and VH were backmutated to obtain humanized antibodies H005-2, H005-3, and H005-4, sequences are as follows.

Antibody Expression

H005-1 HC
SEQ ID NO: 11
EVQLVESGGGLVQPGGSLRLSCAASGFTFSSYMMSWVRQAPGKGLEWVAT

ISGGGANTYYPDSVKGRFTISRDNAKNSLYLQMNSLRAEDTAVYYCARQL

YYFDYWGQGTTVTVSSASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEAAGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK

H005-1 LC
SEQ ID NO: 12
DIQMTQSPSSLSASVGDRVTITCLASQTIGTWLTWYQQKPGKAPKLLIYT

ATSLADGVPSRFSGSGSGTDFTLTISSLQPEDFATYYCQQVYSIPWTFGG

GTKVEIKRTVAASPVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The HC sequence of the humanized antibody H005-1 with grafted murine CDR is (SEQID NO: 11), the LC sequence of the humanized antibody is (SEQ ID NO: 12). Sites which may affect the antibody activity were subjected to point mutations, the sequences are as follows:

|  | HC | LC |
| --- | --- | --- |
| H005-1 | SEQID NO: 11 | SEQID NO: 12 |
| H005-2 | SEQID NO: 11, G44R | SEQID NO: 12 |
| H005-3 | SEQID NO: 11 | SEQID NO: 12, A43S |
| H005-4 | SEQID NO: 11, G44R | SEQID NO: 12, A43S | cDNAs were synthesized according to the amino acid sequences of the light chain and the heavy chain of each humanized antibody (SEQ NO 11, SEQ NO 12 and variants thereof). After the cDNAs were digested with XhoI and BamHI, the obtained cDNA fragments were inserted into pcDNA3.1 expression vectors (Life Technologies Cat. No. V790-20) at BamHI/XhoI restriction sites. The expression vectors and a transfection reagent PEI (Polysciences, Inc. Cat. No. 23966) were used to transfect HEK293 cells (Life Technologies Cat. No. 11625019) at 1:2, and the transfected cells were incubated in a $CO_2$ incubator for 4-5 days. Expressed antibodies were recovered by centrifugation, and purified according to a conventional method to obtain the humanized antibodies of the present invention.

Example 8: Humanized Antibody Activity Data

Humanized antibodies were subjected to ELISA binding assay (method is the same as that of Example 2), ligand binding blocking assay (method is the same as that of Example 2), and affinity kinetics experiment (method is the same as that of Example 5) in vitro. The results are shown in the following table:

| Test Antibody | ELISA, EC50, nM | LBB assay, IC50, nM | KD (M) |
| --- | --- | --- | --- |
| H005-1 | 0.11 | 1.27 | 2.79E−09 |
| H005-2 | 0.14 | 1.27 | 2.98E−09 |
| H005-3 | 0.15 | 1.33 | 2.45E−09 |
| H005-4 | 0.14 | 1.36 | 3.89E−09 |

The result showed that humanized antibodies H005-1, H005-2, H005-3 and H005-4 maintained the PD-1 binding activity, with affinity kinetics KD of 2.79, 2.98, 2.45 and 3.89 nM respectively. Simultaneously, all the humanized antibodies effectively exhibited blocking activity against the PD-L1/PD-1 pathway.

Example 9: Tumor Cell Growth Inhibition by PD-1 Antibody

1. Experimental Materials:

U87MG cells (glioma cells): purchased from the Chinese Academy of Sciences Cell Bank, Cat. TCHu138;

PBMCs (peripheral blood mononuclear cells) purchased from the Shanghai Blood Center;

CD3: purchased from Miltenyi Biotec Cat No. 130-093-387;

CD28: purchased from Miltenyi Biotec Cat No. 130-093-375;

Cell Counting Kit-8: available from DOJINDO LABORATORIES, Cat No. CK04;

mIgG (negative control): purchased from SANTA CRUZ Cat No. sc-2025; using dose of 1660 ng/ml.

2. Experimental Methods:

1) U87MG cells were cultured in EMEM medium containing 10% FBS and 1% P/S, incubated in a 96-well plate, $1 \times 10^4$ cells per well.

2) H005-1 antibody was diluted to different concentration gradients (shown in abscissa of FIG. 3) with PBS, added to the 96-well plate at 10 ul/well, and incubated in 37° C., 5% $CO_2$ incubator for 4 hours.

3) After cell adherence, 80 ul of PBMC cell suspension was added to each well with a cell density of $2 \times 10^4$ cells/well, and 10 ul of CD3 antibody and CD28 antibody were added in each well, the final concentrations of CD3 and CD28 antibodies were both 500 ng/ml. 4) After 72 hours of incubation in the 37° C., 5% $CO_2$ incubator, 10 ul of CCK8 was added to each well for development. 2 hours later, OD450 was determinated.

Figure 3:
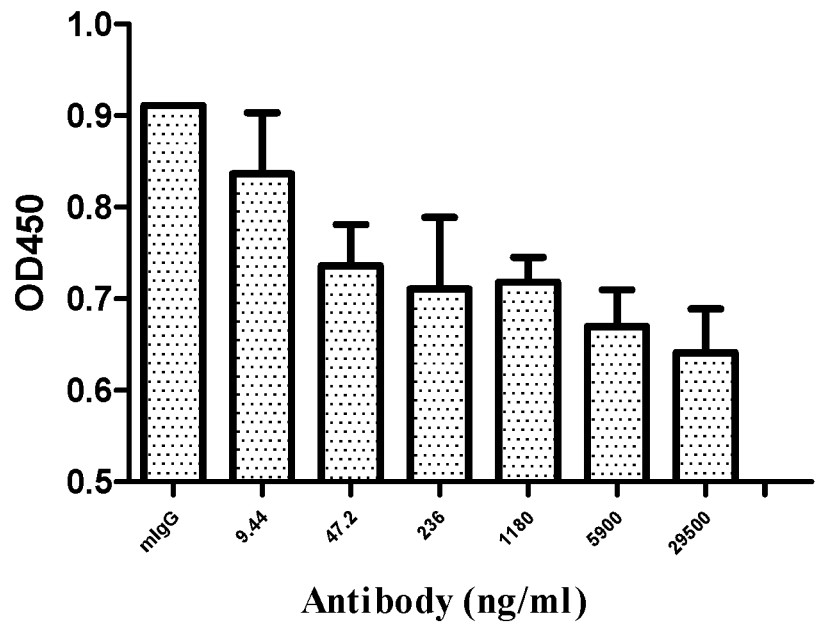
FIG. 3: inhibitory effect of PD-1 antibody H005-1 on growth of glioma cells.

3. Result:

The result was shown in FIG. 3, as compared with mIgG (negative control), different concentrations of PD-1 antibody (H005-1) had significant inhibitory effect on U87MG cell growth, and inhibition rate at the highest concentration was about 30%.

Example 10: Activity of H005-1 on Tuberculin-Stimulated PBMC Proliferation

The activity of the humanized antibody H005-1 on tuberculin-stimulated PBMC proliferation in vitro was detected.

To 15 ml of fresh PBMCs, about $3\times10^7$ cells, were added 20 μl tuberculin (Shanghai BiYou Biotechnology, cat #97-8800) and the mixture were incubated for 5 days in the 37° C., 5% $CO_2$ incubator. On day 6, the cultured cells were centrifugated, and resuspended into fresh medium with a density adjusted to $5\times10^5$ cells/ml. 190 μl of resuspended cells was planted into each well of a 96-well plate. The humanized antibody H005-1 was added to corresponding wells of the 96-well plate at 10 μl/well. The control group and blank group were added with 10 μl of PBS. The Cell culture plate was incubated in the 37° C., 5% $CO_2$ incubator, and 72 hours later, PBMC Proliferation (Promega, cat #G7571) and IFN-γ secretion (Neo Bioscience, cat #EHC102 g) were determined. The results are as follows:

Activation Effect of the Test Sample on Tuberculin Stimulated PBMC Proliferation and IFN-γ Secretion

| Sample | T cell proliferation EC50 (ng/ml) | IFN-λ EC50 (ng/ml) |
|---|---|---|
| H005-1 | 15.95 ± 17.15 | 56.87 ± 48.53 |

Note:
n = 4

Experiment results showed that the humanized antibody H005-1 excellently activates exogenous tuberculin stimulated PBMC proliferation and IFN-γ secretion.

Example 11: Inhibition of Subcutaneously Inoculated U-87MG Tumor by H005-1

100 ul of U87 cells ($5\times10^6$ cells) was inoculated subcutaneously in right ribs of SCID-Beige mice. When the tumor grew to 80-100 mm$^3$ after 7 to 10 days, the SCID-Beige mice, getting rid of ones with too large or too small body weight or tumor, were randomly divided into a H005-1 10 mg/kg group and a Human IgG 10 mg/kg group according to the tumor volume, each group of seven mice (DO). Two kinds of PBMCs stimulated by CD3 antibody for 3 days were mixed at a ratio of 1:1, and injected into the tumor tissues at $5\times10^5$ cells/60 ul, meanwhile, the test antibody was injected subcutaneously, once per 7 days for total 3 doses. Mice were measured for tumor volume and weighed twice a week. Data was recorded. Tumor volume (V) was calculated as: $V=\frac{1}{2}\times a\times b2$, wherein a and b represented length and width, respectively.

Figure 4:
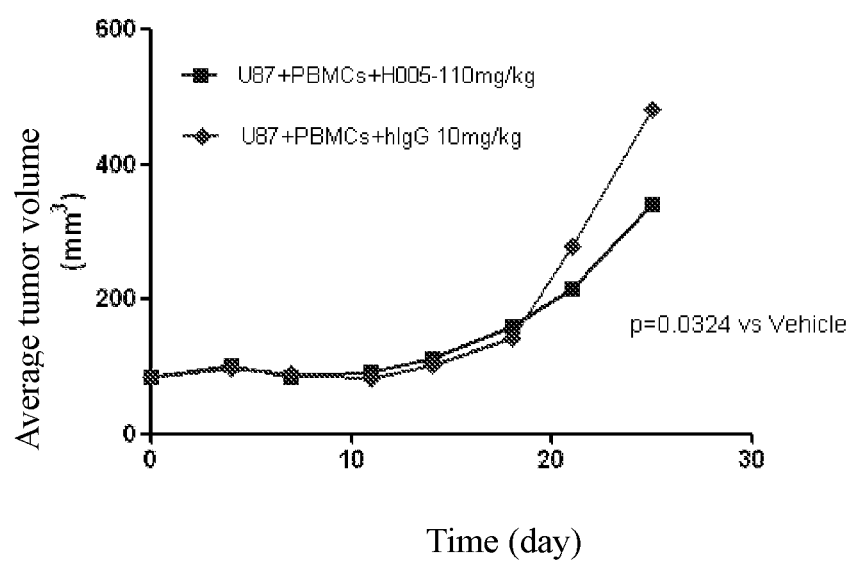
FIG. 4: diagram showing tumor volume change after treatment.
Figure 5:
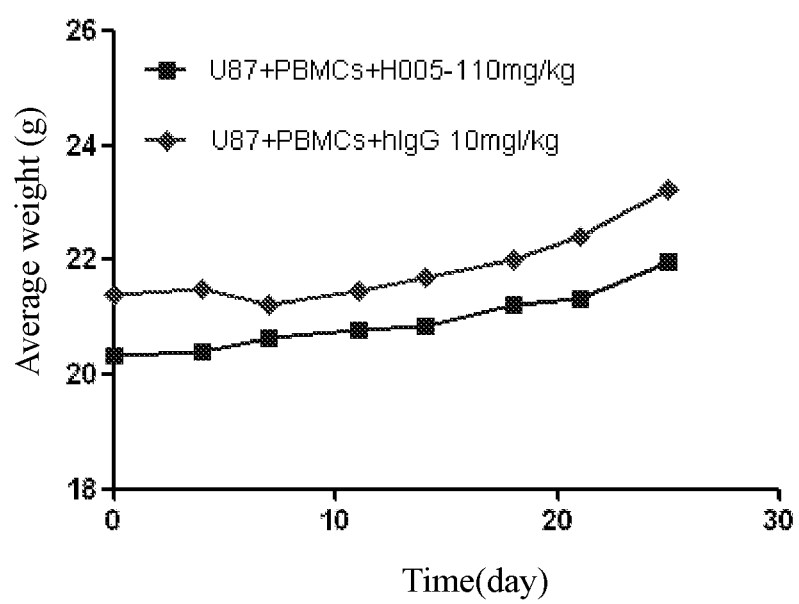
FIG. 5: diagram showing weight change of mice after treatment.

The result was shown in FIG. 4: tumor volume change after treatment, and FIG. 5: mice weight change after treatment, indicating that antibody H005-1 excellently inhibited U87MG tumor growth, and had no effect on the body weight of the mice.

It is claimed:

1. An anti-PD1 antibody or an antigen-binding fragment thereof, comprising a light chain variable region and a heavy chain variable region, wherein the anti-PD1 antibody or the antigen-binding fragment thereof specifically binds to a human or cynomolgus PD1 polypeptide, and wherein the heavy chain variable region comprises complementarity determining regions (CDRs) comprising the amino acid sequences of the corresponding CDRs of the antibody heavy chain of SEQ ID NO: 11, and wherein the light chain variable region comprises CDRs comprising the amino acid sequences of the corresponding CDRs of the antibody light chain of SEQ ID NO: 12.

2. The anti-PD1 antibody or the antigen-binding fragment thereof according to claim 1, (i) wherein the light chain variable region comprises the amino acid sequence of amino acids 1-107 of SEQ ID NO: 12 or the light chain variable region comprises the amino acid sequence of amino acids 1-107 of SEQ ID NO: 12 but for the replacement of the amino acid at position 43 (alanine) with serine (A43S), wherein the positions of the amino acid replacement is according to Kabat numbering; and (ii) wherein the heavy chain variable region comprises the amino acid sequence of amino acids 1-116 of SEQ ID NO: 11 or the heavy chain variable region comprises the amino acid sequence of amino acids 1-116 of SEQ ID NO: 11 but for the replacement of the amino acid at position 44 (glycine) with arginine (G44R), wherein the positions of the amino acid replacement is according to Kabat numbering.

3. The anti-PD1 antibody or the antigen-binding fragment thereof according to claim 1, wherein the antibody further comprises a light chain constant region of human κ or λ chain and a heavy chain constant region of human IgG1, human IgG2, human IgG3, human IgG4, or a variant of the heavy chain constant region selected from the group consisting of: (a) a variant of the heavy chain constant region of a human IgG1 in which one or more of the amino acids at positions 297, 234, and 235, as according to EU numbering, have been replaced by alanine; (b) a variant of the heavy chain constant region of a human IgG4 in which the amino acid at position 235, as according to EU numbering, has been replaced by glutamic acid; or (c) a variant of the heavy chain constant region of a human IgG4 in which the amino acids at positions 234 and 235, as according to EU numbering, have been replaced by alanine.

4. The anti-PD1 antibody or the antigen-binding fragment thereof according to claim 1, wherein the antibody comprises a light chain having the amino acid sequence of SEQ ID NO: 12 or a light chain having the amino acid sequence of SEQ ID NO: 12 but for the replacement of the amino acid at position 43 (alanine) with serine (A43S); and a heavy chain having the amino acid sequence of SEQ ID NO: 11 or a heavy chain having the amino acid sequence of SEQ ID NO: 11 but for the replacement of the amino acid at position 44 (glycine) with arginine (G44R), wherein the positions of the amino acid replacements are according to Kabat numbering.

5. A DNA molecule encoding the antibody or the antigen-binding fragment thereof according to claim 1.

6. An expression vector comprising the DNA molecule according to claim 5.

7. A host cell transformed with the expression vector according to claim 6.

8. The host cell according to claim 7, wherein the host cell is a bacteria cell or a yeast cell.

9. A pharmaceutical composition comprising the antibody or the antigen-binding fragment thereof according to claim 1 and a pharmaceutically acceptable excipient, diluent or carrier.

10. A method for treating cancer in a human subject, the method comprising administering to the subject an effective amount of the antibody according to claim 1 to block binding of PD-1 to PD-L1 in the subject.

11. The method of claim 10, wherein the cancer is selected from the group consisting of breast cancer, lung cancer, stomach cancer, intestinal cancer, renal cancer, melanoma and non-small cell lung cancer.

12. An anti-PD-1 antibody or an antigen-binding fragment thereof, comprising a light chain variable region and a heavy chain variable region, wherein the anti-PD-1 antibody or the antigen-binding fragment thereof specifically binds to a human or cynomolgus PD-1 polypeptide, wherein the light chain variable region comprises the amino acid sequence of amino acids 1-107 of SEQ ID NO: 12 and wherein the heavy chain variable region comprises the amino acid sequence of amino acids 1-116 of SEQ ID NO: 11.

* * * * *

SEQUENCE LISTING

```
<160> NUMBER OF SEQ ID NOS: 14

<210> SEQ ID NO 1
<211> LENGTH: 399
<212> TYPE: PRT
<213> ORGANISM: Artificial Sequence
<220> FEATURE:
<223> OTHER INFORMATION: recombinant PD-1 extracellular domain Fc fusion
      protein

<400> SEQUENCE: 1

Met Asp Met Arg Val Pro Ala Gln Leu Leu Gly Leu Leu Leu Leu Trp
1               5                   10                  15

Phe Pro Gly Ser Arg Cys Pro Gly Trp Phe Leu Asp Ser Pro Asp Arg
                20                  25                  30

Pro Trp Asn Pro Pro Thr Phe Ser Pro Ala Leu Leu Val Val Thr Glu
            35                  40                  45

Gly Asp Asn Ala Thr Phe Thr Cys Ser Phe Ser Asn Thr Ser Glu Ser
        50                  55                  60

Phe Val Leu Asn Trp Tyr Arg Met Ser Pro Ser Asn Gln Thr Asp Lys
65                  70                  75                  80

Leu Ala Ala Phe Pro Glu Asp Arg Ser Gln Pro Gly Gln Asp Cys Arg
                85                  90                  95

Phe Arg Val Thr Gln Leu Pro Asn Gly Arg Asp Phe His Met Ser Val
                100                 105                 110
```

-continued

Val Arg Ala Arg Arg Asn Asp Ser Gly Thr Tyr Leu Cys Gly Ala Ile
            115                 120                 125

Ser Leu Ala Pro Lys Ala Gln Ile Lys Glu Ser Leu Arg Ala Glu Leu
130                 135                 140

Arg Val Thr Glu Arg Arg Ala Glu Val Pro Thr Ala His Pro Ser Pro
145                 150                 155                 160

Ser Pro Arg Pro Ala Gly Gln Phe Gln Thr Leu Val Asp Lys Thr His
                165                 170                 175

Thr Cys Pro Pro Cys Pro Ala Pro Glu Leu Leu Gly Gly Pro Ser Val
            180                 185                 190

Phe Leu Phe Pro Pro Lys Pro Lys Asp Thr Leu Met Ile Ser Arg Thr
195                 200                 205

Pro Glu Val Thr Cys Val Val Val Asp Val Ser His Glu Asp Pro Glu
210                 215                 220

Val Lys Phe Asn Trp Tyr Val Asp Gly Val Glu Val His Asn Ala Lys
225                 230                 235                 240

Thr Lys Pro Arg Glu Glu Gln Tyr Asn Ser Thr Tyr Arg Val Val Ser
                245                 250                 255

Val Leu Thr Val Leu His Gln Asp Trp Leu Asn Gly Lys Glu Tyr Lys
            260                 265                 270

Cys Lys Val Ser Asn Lys Ala Leu Pro Ala Pro Ile Glu Lys Thr Ile
        275                 280                 285

Ser Lys Ala Lys Gly Gln Pro Arg Glu Pro Gln Val Tyr Thr Leu Pro
290                 295                 300

Pro Ser Arg Glu Glu Met Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Lys Leu Thr Val Asp Lys Ser Arg
        355                 360                 365

Trp Gln Gln Gly Asn Val Phe Ser Cys Ser Val Met His Glu Ala Leu
370                 375                 380

His Asn His Tyr Thr Gln Lys Ser Leu Ser Leu Ser Pro Gly Lys
385                 390                 395

<210> SEQ ID NO 2
<211> LENGTH: 288
<212> TYPE: PRT
<213> ORGANISM: Homo sapiens

<400> SEQUENCE: 2

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

```
Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
            165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
            245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285
```

<210> SEQ ID NO 3
<211> LENGTH: 5
<212> TYPE: PRT
<213> ORGANISM: Mus musculus

<400> SEQUENCE: 3

```
Ser Tyr Met Met Ser
1               5
```

<210> SEQ ID NO 4
<211> LENGTH: 17
<212> TYPE: PRT
<213> ORGANISM: Mus musculus

<400> SEQUENCE: 4

```
Thr Ile Ser Gly Gly Gly Ala Asn Thr Tyr Tyr Pro Asp Ser Val Lys
1               5                   10                  15

Gly
```

<210> SEQ ID NO 5
<211> LENGTH: 7
<212> TYPE: PRT
<213> ORGANISM: Mus musculus

<400> SEQUENCE: 5

```
Gln Leu Tyr Tyr Phe Asp Tyr
1               5
```

<210> SEQ ID NO 6
<211> LENGTH: 11
<212> TYPE: PRT
<213> ORGANISM: Mus musculus

<400> SEQUENCE: 6

```
Leu Ala Ser Gln Thr Ile Gly Thr Trp Leu Thr
1               5                   10

<210> SEQ ID NO 7
<211> LENGTH: 7
<212> TYPE: PRT
<213> ORGANISM: Mus musculus

<400> SEQUENCE: 7

Thr Ala Thr Ser Leu Ala Asp
1               5

<210> SEQ ID NO 8
<211> LENGTH: 9
<212> TYPE: PRT
<213> ORGANISM: Mus musculus

<400> SEQUENCE: 8

Gln Gln Val Tyr Ser Ile Pro Trp Thr
1               5

<210> SEQ ID NO 9
<211> LENGTH: 116
<212> TYPE: PRT
<213> ORGANISM: Mus musculus

<400> SEQUENCE: 9

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Met Met Ser Trp Val Arg Gln Thr Pro Glu Lys Arg Leu Glu Trp Val
        35                  40                  45

Ala Thr Ile Ser Gly Gly Gly Ala Asn Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Gln Leu Tyr Tyr Phe Asp Tyr Trp Gly Gln Gly Thr Thr Leu
            100                 105                 110

Thr Val Ser Ser
        115

<210> SEQ ID NO 10
<211> LENGTH: 107
<212> TYPE: PRT
<213> ORGANISM: Mus musculus

<400> SEQUENCE: 10

Asp Ile Gln Met Thr Gln Ser Pro Ala Ser Gln Ser Ala Ser Leu Gly
1               5                   10                  15

Glu Gly Val Thr Ile Thr Cys Leu Ala Ser Gln Thr Ile Gly Thr Trp
            20                  25                  30

Leu Thr Trp Tyr Gln Gln Lys Pro Gly Lys Ser Pro Gln Leu Leu Ile
        35                  40                  45

Tyr Thr Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
```

```
                65                  70                  75                  80
Glu Asp Phe Val Thr Tyr Tyr Cys Gln Gln Val Tyr Ser Ile Pro Trp
                    85                  90                  95

Thr Phe Gly Gly Gly Thr Lys Leu Glu Ile Lys
            100                 105

<210> SEQ ID NO 11
<211> LENGTH: 443
<212> TYPE: PRT
<213> ORGANISM: Artificial sequence
<220> FEATURE:
<223> OTHER INFORMATION: heavy chain sequence of humanized antibody
      H005-1

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Met Met Ser Trp Val Arg Gln Ala Pro Gly Lys Gly Leu Glu Trp Val
            35                  40                  45

Ala Thr Ile Ser Gly Gly Gly Ala Asn Thr Tyr Tyr Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Tyr Phe Asp Tyr Trp Gly Gln Gly Thr Thr Val
                100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320
```

```
Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
            435                 440
```

<210> SEQ ID NO 12
<211> LENGTH: 214
<212> TYPE: PRT
<213> ORGANISM: Artificial sequence
<220> FEATURE:
<223> OTHER INFORMATION: light chain sequence of humanized antibody H005-1

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Thr Trp Tyr Gln Gln Lys Pro Gly Lys Ala Pro Lys Leu Leu Ile
            35                  40                  45

Tyr Thr Ala Thr Ser Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Val Tyr Ser Ile Pro Trp
            85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 13

```
<211> LENGTH: 109
<212> TYPE: PRT
<213> ORGANISM: Artificial sequence
<220> FEATURE:
<223> OTHER INFORMATION: heavy chain framework region sequence of
      humanized antibody

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Thr Val Thr Val Ser Ser
            100                 105

<210> SEQ ID NO 14
<211> LENGTH: 98
<212> TYPE: PRT
<213> ORGANISM: Artificial sequence
<220> FEATURE:
<223> OTHER INFORMATION: light chain framework region sequence of
      humanized antibody

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gly Gly Gly Thr Lys Val Glu
                85                  90                  95

Ile Lys
```